US008153602B1

(12) United States Patent
Bennett et al.

(10) Patent No.: US 8,153,602 B1
(45) Date of Patent: Apr. 10, 2012

(54) COMPOSITION AND METHODS FOR THE PULMONARY DELIVERY OF NUCLEIC ACIDS

(75) Inventors: Clarence Frank Bennett, Carlsbad, CA (US); David J. Ecker, Encinitas, CA (US); Phillip Dan Cook, Fallbrook, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/315,292

(22) Filed: May 20, 1999

Related U.S. Application Data

(63) Continuation-in-part of application No. 09/083,586, filed on May 21, 1998, now abandoned, and a continuation-in-part of application No. 09/083,585, filed on May 21, 1998, now abandoned, which is a continuation-in-part of application No. 07/794,396, filed on Nov. 19, 1991, now Pat. No. 6,034,233, and a continuation-in-part of application No. 08/227,180, filed on Apr. 13, 1994, now Pat. No. 5,866,698, which is a continuation-in-part of application No. 07/801,168, filed on Nov. 29, 1991, now abandoned.

(51) Int. Cl.
*A61K 48/00* (2006.01)
*C07H 21/04* (2006.01)
*C07H 21/02* (2006.01)

(52) U.S. Cl. ... 514/44; 536/23.1; 536/24.31; 536/24.33; 536/24.5

(58) Field of Classification Search ............. 435/6, 69.1, 435/91.1, 440, 325, 352, 354, 366, 371, 91.2; 514/44; 536/23.1, 23.5, 24.31, 24.5
See application file for complete search history.

(56) References Cited

U.S. PATENT DOCUMENTS

| | | | |
|---|---|---|---|
| 3,687,808 A | 8/1972 | Merigan et al. | 195/28 |
| 4,415,732 A | 11/1983 | Caruthers et al. | 536/27 |
| 4,458,066 A | 7/1984 | Caruthers et al. | 536/27 |
| 4,469,863 A | 9/1984 | Ts'o et al. | 536/27 |
| 4,476,301 A | 10/1984 | Imbach et al. | 536/27 |
| 4,500,707 A | 2/1985 | Caruthers et al. | 536/27 |
| 4,501,729 A | 2/1985 | Boucher et al. | 424/45 |
| 4,587,044 A | 5/1986 | Miller et al. | 530/211 |
| 4,605,735 A | 8/1986 | Miyoshi et al. | 536/27 |
| 4,667,025 A | 5/1987 | Miyoshi et al. | 536/27 |
| 4,668,777 A | 5/1987 | Caruthers et al. | 536/27 |
| 4,689,320 A | 8/1987 | Kaji | 514/44 |
| 4,725,677 A | 2/1988 | Köster et al. | 536/27 |
| 4,762,779 A | 8/1988 | Snitman | 435/6 |
| 4,789,737 A | 12/1988 | Miyoshi et al. | 536/27 |
| 4,806,463 A | 2/1989 | Goodchild et al. | 435/5 |
| 4,824,941 A | 4/1989 | Gordon et al. | 530/403 |
| 4,828,979 A | 5/1989 | Klevan et al. | 435/6 |
| 4,835,263 A | 5/1989 | Nguyen et al. | 536/27 |
| 4,845,205 A | 7/1989 | Huynh Dinh et al. | 536/28 |
| 4,876,335 A | 10/1989 | Yamane et al. | 536/27 |
| 4,904,582 A | 2/1990 | Tullis | 435/6 |
| 4,948,882 A | 8/1990 | Ruth | 536/27 |
| 4,958,013 A | 9/1990 | Letsinger | 536/27 |
| 4,973,679 A | 11/1990 | Caruthers et al. | 536/27 |
| 4,981,957 A | 1/1991 | Lebleu et al. | 536/27 |
| 5,004,810 A | 4/1991 | Draper | 536/27 |
| 5,013,830 A | 5/1991 | Ohtsuka et al. | 536/27 |
| 5,023,243 A | 6/1991 | Tullis | 514/44 |
| 5,034,506 A | 7/1991 | Summerton et al. | 528/391 |
| 5,082,830 A | 1/1992 | Brakel et al. | 514/44 |
| 5,087,617 A | 2/1992 | Smith | 514/44 |
| 5,098,890 A | 3/1992 | Gewirtz et al. | 514/44 |
| 5,109,124 A | 4/1992 | Ramachandran et al. | 536/27 |
| 5,112,963 A | 5/1992 | Pieles et al. | 536/27 |
| 5,118,800 A | 6/1992 | Smith et al. | 536/23 |
| 5,118,802 A | 6/1992 | Smith et al. | 536/27 |
| 5,130,302 A | 7/1992 | Spielvogel et al. | 514/45 |
| 5,132,418 A | 7/1992 | Caruthers et al. | 536/27 |
| 5,134,066 A | 7/1992 | Rogers et al. | 435/91 |
| 5,135,917 A | 8/1992 | Burch | 514/44 |
| 5,138,045 A | 8/1992 | Cook et al. | 536/27 |
| RE34,069 E | 9/1992 | Köster et al. | 536/27 |
| 5,149,797 A | 9/1992 | Pederson et al. | 536/27 |
| 5,166,195 A | 11/1992 | Ecker | 514/44 |
| 5,166,315 A | 11/1992 | Summerton et al. | 528/406 |
| 5,175,273 A | 12/1992 | Bischofberger et al. | 536/27 |
| 5,177,196 A | 1/1993 | Meyer, Jr. et al. | 536/27.1 |
| 5,177,198 A | 1/1993 | Spielvogel et al. | 536/25.33 |
| 5,185,444 A | 2/1993 | Summerton et al. | 544/81 |
| 5,188,897 A | 2/1993 | Suhadolnik et al. | 428/402.2 |

(Continued)

FOREIGN PATENT DOCUMENTS

WO    WO 93/19203    9/1993

(Continued)

OTHER PUBLICATIONS

Milligan, J.F. et al. Journal of Medicinal Chemistry. vol. 36 (14), Jul. 1993, pp. 1923-1937.*
Tereshko et al., Correlating Structure and Stability of DNA Duplexes with Incorporated 2'-O-Modified RNA Analogues, 1998, Biochemistry, 37, 10626-10634.*
Milligan et al., Current Concepts in Antisense Drug Design, Jul. 1993, Journal of Medicinal Chemistry, vol. 36, No. 14, pp. 1923-1937.*
Clark, Medical Aerosol Inhalers: Past, Present, and Future, 1995, Aerosol Science and Technology, 22, pp. 374-391.*

(Continued)

*Primary Examiner* — Amy Bowman
(74) *Attorney, Agent, or Firm* — Isis Pharmaceuticals, Inc. Patent Department

(57) ABSTRACT

The present invention relates to compositions and methods for the pulmonary delivery of nucleic acids, particularly oligonucleotides. In one preferred embodiment, the compositions and methods of the invention are utilized to effect the pulmonary delivery of an antisense oligonucleotide to an animal in order to modulate the expression of a gene in the animal for investigative, therapeutic or prophylactic purposes.

11 Claims, 2 Drawing Sheets

U.S. PATENT DOCUMENTS

| | | | | |
|---|---|---|---|---|
| 5,194,428 A | 3/1993 | Agrawal et al. .................. 514/44 |
| 5,212,295 A | 5/1993 | Cook ............................ 536/26.7 |
| 5,214,134 A | 5/1993 | Weis et al. .................... 536/25.3 |
| 5,214,136 A | 5/1993 | Lin et al. ......................... 514/44 |
| 5,216,141 A | 6/1993 | Benner ....................... 536/27.13 |
| 5,218,105 A | 6/1993 | Cook et al. ................. 536/25.31 |
| 5,220,007 A | 6/1993 | Pederson et al. .............. 536/23.1 |
| 5,223,618 A | 6/1993 | Cook et al. ...................... 544/276 |
| 5,235,033 A | 8/1993 | Summerton et al. ........... 528/391 |
| 5,242,906 A | 9/1993 | Pagano et al. ................... 514/44 |
| 5,245,022 A | 9/1993 | Weis et al. .................... 536/24.5 |
| 5,254,469 A | 10/1993 | Warren, III et al. ........... 435/188 |
| 5,256,775 A | 10/1993 | Froehler ....................... 536/25.6 |
| 5,258,506 A | 11/1993 | Urdea ........................... 536/23.1 |
| 5,262,536 A | 11/1993 | Hobbs, Jr. ........................ 546/25 |
| 5,264,423 A | 11/1993 | Cohen et al. ..................... 514/44 |
| 5,264,562 A | 11/1993 | Matteucci ..................... 536/23.1 |
| 5,264,564 A | 11/1993 | Matteucci ..................... 536/23.1 |
| 5,272,250 A | 12/1993 | Spielvogel et al. ........... 530/300 |
| 5,276,019 A | 1/1994 | Cohen et al. ..................... 514/44 |
| 5,278,302 A | 1/1994 | Caruthers et al. ............. 536/24.5 |
| 5,286,717 A | 2/1994 | Cohen et al. ..................... 514/44 |
| 5,292,873 A | 3/1994 | Rokita et al. .................. 536/24.3 |
| 5,317,098 A | 5/1994 | Shizuya et al. ............... 536/23.1 |
| 5,319,080 A | 6/1994 | Leumann ...................... 536/27.1 |
| 5,321,131 A | 6/1994 | Agrawal et al. .............. 536/25.34 |
| 5,359,044 A | 10/1994 | Cook et al. .................... 536/23.1 |
| 5,366,878 A | 11/1994 | Pederson et al. ............. 435/91.3 |
| 5,367,066 A | 11/1994 | Urdea et al. ................... 536/24.3 |
| 5,371,241 A | 12/1994 | Brush ............................ 549/220 |
| 5,378,825 A | 1/1995 | Cook et al. .................. 536/25.34 |
| 5,386,023 A | 1/1995 | Sanghvi et al. ............... 536/25.3 |
| 5,391,723 A | 2/1995 | Priest ............................. 536/23.1 |
| 5,393,878 A | 2/1995 | Leumann ...................... 536/28.2 |
| 5,399,676 A | 3/1995 | Froehler ........................ 536/23.1 |
| 5,403,711 A | 4/1995 | Walder et al. ....................... 435/6 |
| 5,405,938 A | 4/1995 | Summerton et al. ........... 528/406 |
| 5,405,939 A | 4/1995 | Suhadolnik et al. ........... 530/322 |
| 5,414,077 A | 5/1995 | Lin et al. ....................... 536/24.3 |
| 5,416,203 A | 5/1995 | Letsinger .................... 536/25.34 |
| 5,432,272 A | 7/1995 | Benner ......................... 536/25.3 |
| 5,434,257 A | 7/1995 | Matteucci et al. ............ 536/24.3 |
| 5,446,137 A | 8/1995 | Maag et al. ................... 536/23.1 |
| 5,451,463 A | 9/1995 | Nelson et al. ................. 428/402 |
| 5,453,496 A | 9/1995 | Caruthers et al. ............. 536/24.5 |
| 5,455,233 A | 10/1995 | Spielvogel et al. .............. 514/44 |
| 5,457,187 A | 10/1995 | Gmeiner et al. .............. 536/25.5 |
| 5,459,255 A | 10/1995 | Cook et al. .................. 536/27.13 |
| 5,466,677 A | 11/1995 | Baxter et al. ..................... 514/44 |
| 5,466,786 A | 11/1995 | Buhr et al. ................... 536/26.26 |
| 5,470,967 A | 11/1995 | Huie et al. .................... 536/24.3 |
| 5,476,925 A | 12/1995 | Letsinger et al. ............. 536/23.1 |
| 5,484,908 A | 1/1996 | Froehler et al. ............. 536/24.31 |
| 5,486,603 A | 1/1996 | Buhr .............................. 536/24.3 |
| 5,489,677 A | 2/1996 | Sanghvi et al. ............... 536/22.1 |
| 5,491,133 A | 2/1996 | Walder et al. .................... 514/44 |
| 5,502,177 A | 3/1996 | Matteucci et al. ............ 536/26.6 |
| 5,506,351 A | 4/1996 | McGee ......................... 536/55.3 |
| 5,508,270 A | 4/1996 | Baxter et al. ..................... 514/47 |
| 5,510,475 A | 4/1996 | Agrawal et al. ............... 536/24.3 |
| 5,512,439 A | 4/1996 | Hornes et al. ...................... 435/6 |
| 5,512,667 A | 4/1996 | Reed et al. .................. 536/24.31 |
| 5,514,785 A | 5/1996 | Van Ness et al. ............. 536/22.1 |
| 5,514,788 A | 5/1996 | Bennett et al. ................ 536/23.1 |
| 5,519,126 A | 5/1996 | Hecht ............................ 536/24.3 |
| 5,519,134 A | 5/1996 | Acevedo et al. .............. 544/243 |
| 5,521,302 A | 5/1996 | Cook .......................... 536/25.31 |
| 5,525,465 A | 6/1996 | Haralambidis et al. ........... 435/6 |
| 5,525,711 A | 6/1996 | Hawkins et al. .............. 536/22.1 |
| 5,536,821 A | 7/1996 | Agrawal et al. .............. 536/22.1 |
| 5,539,082 A | 7/1996 | Nielsen et al. ................ 530/300 |
| 5,539,083 A | 7/1996 | Cook et al. .................... 530/333 |
| 5,541,306 A | 7/1996 | Agrawal et al. .............. 536/22.1 |
| 5,541,307 A | 7/1996 | Cook et al. .................... 536/23.1 |
| 5,541,313 A | 7/1996 | Ruth .............................. 536/24.3 |
| 5,543,508 A | 8/1996 | Haseloff et al. ............... 536/23.2 |
| 5,545,729 A | 8/1996 | Goodchild et al. ............ 536/24.5 |
| 5,545,730 A | 8/1996 | Urdea et al. ................. 536/28.51 |
| 5,550,111 A | 8/1996 | Suhadolnik et al. ............. 514/44 |
| 5,552,538 A | 9/1996 | Urdea et al. ................... 536/24.3 |
| 5,552,540 A | 9/1996 | Haralambidis ............. 536/25.34 |
| 5,554,746 A * | 9/1996 | Ravikumar et al. ........... 540/200 |
| 5,561,225 A | 10/1996 | Maddry et al. ................ 536/23.1 |
| 5,563,253 A | 10/1996 | Agrawal et al. ............... 536/22.1 |
| 5,565,350 A | 10/1996 | Kmiec ........................ 435/172.3 |
| 5,565,552 A | 10/1996 | Magda et al. .................... 534/11 |
| 5,567,810 A | 10/1996 | Weis et al. ..................... 536/25.3 |
| 5,567,811 A | 10/1996 | Misiura et al. .............. 536/25.34 |
| 5,571,799 A | 11/1996 | Tkachuk et al. .................. 514/47 |
| 5,574,142 A | 11/1996 | Meyer, Jr. et al. ............. 536/23.1 |
| 5,576,427 A | 11/1996 | Cook et al. .................... 536/23.1 |
| 5,578,717 A | 11/1996 | Urdea et al. ................... 536/26.1 |
| 5,578,718 A | 11/1996 | Cook et al. ............... 536/717.21 |
| 5,580,731 A | 12/1996 | Chang et al. ...................... 435/6 |
| 5,582,972 A | 12/1996 | Lima et al. ........................ 435/6 |
| 5,582,986 A | 12/1996 | Monia et al. ...................... 435/6 |
| 5,585,481 A | 12/1996 | Arnold, Jr. et al. .......... 536/25.33 |
| 5,587,361 A | 12/1996 | Cook et al. ....................... 514/44 |
| 5,587,371 A | 12/1996 | Sessler et al. ................. 514/185 |
| 5,587,469 A | 12/1996 | Cook et al. .................... 536/23.1 |
| 5,591,584 A | 1/1997 | Chang et al. ...................... 435/6 |
| 5,591,623 A | 1/1997 | Bennett et al. .............. 435/240.2 |
| 5,591,722 A | 1/1997 | Montgomery et al. .......... 514/45 |
| 5,594,121 A | 1/1997 | Froehler et al. ............... 536/23.5 |
| 5,595,726 A | 1/1997 | Magda et al. ................. 424/9.61 |
| 5,595,978 A | 1/1997 | Draper et al. .................... 514/44 |
| 5,596,086 A | 1/1997 | Matteucci et al. ............ 536/22.1 |
| 5,596,091 A | 1/1997 | Switzer ......................... 536/24.5 |
| 5,597,696 A | 1/1997 | Linn et al. ......................... 435/6 |
| 5,597,909 A | 1/1997 | Urdea et al. ................... 536/24.3 |
| 5,599,923 A | 2/1997 | Sessler et al. ................. 540/145 |
| 5,599,928 A | 2/1997 | Hemmi et al. ................ 540/474 |
| 5,602,240 A | 2/1997 | De Mesmaeker et al. ... 536/22.1 |
| 5,608,046 A | 3/1997 | Cook et al. .................... 536/23.1 |
| 5,610,289 A | 3/1997 | Cook et al. .................. 536/25.34 |
| 5,610,300 A | 3/1997 | Altmann et al. ............... 544/244 |
| 5,614,617 A | 3/1997 | Cook et al. .................... 536/23.1 |
| 5,618,704 A | 4/1997 | Sanghvi et al. .............. 435/91.5 |
| 5,620,963 A | 4/1997 | Cook et al. ....................... 514/44 |
| 5,623,065 A | 4/1997 | Cook et al. .................... 536/23.1 |
| 5,623,070 A | 4/1997 | Cook et al. .................... 536/27.6 |
| 5,625,050 A | 4/1997 | Beaton et al. ................. 536/24.1 |
| 5,627,053 A | 5/1997 | Usman et al. ................ 435/91.1 |
| 5,627,274 A * | 5/1997 | Kole et al. ..................... 536/23.1 |
| 5,633,360 A | 5/1997 | Bischofberger et al. ..... 536/22.1 |
| 5,639,873 A | 6/1997 | Barascut et al. ............... 536/25.3 |
| 5,641,662 A * | 6/1997 | Debs et al. .................. 435/172.1 |
| 5,646,265 A | 7/1997 | McGee ....................... 536/25.34 |
| 5,652,355 A | 7/1997 | Metelev et al. ............... 536/24.5 |
| 5,652,356 A | 7/1997 | Agrawal ....................... 536/24.5 |
| 5,658,873 A | 8/1997 | Bertsch-Frank et al. ..... 510/375 |
| 5,661,134 A | 8/1997 | Cook et al. ....................... 514/44 |
| 5,663,312 A | 9/1997 | Chaturvedula ............... 536/22.1 |
| 5,670,633 A | 9/1997 | Cook et al. .................... 536/23.1 |
| 5,677,437 A | 10/1997 | Teng et al. ..................... 536/23.1 |
| 5,677,439 A | 10/1997 | Weis et al. ..................... 536/23.1 |
| 5,681,747 A | 10/1997 | Boggs et al. .................... 435/375 |
| 5,681,941 A | 10/1997 | Cook et al. .................... 536/23.1 |
| 5,688,941 A | 11/1997 | Cook et al. .................... 536/25.3 |
| 5,697,248 A | 12/1997 | Brown ............................. 73/290 |
| 5,700,920 A | 12/1997 | Altmann et al. ............... 536/221 |
| 5,700,922 A | 12/1997 | Cook ............................. 536/23.1 |
| 5,714,331 A | 2/1998 | Buchardt et al. .................. 435/6 |
| 5,716,780 A | 2/1998 | Edwards et al. ................... 435/6 |
| 5,719,262 A | 2/1998 | Buchardt et al. .............. 530/300 |
| 5,733,572 A * | 3/1998 | Unger et al. ................... 424/450 |
| 5,789,573 A * | 8/1998 | Baker et al. ................... 536/24.5 |
| 5,801,154 A * | 9/1998 | Baracchini et al. .............. 514/44 |
| 5,858,784 A * | 1/1999 | Debs et al. ..................... 435/375 |
| 5,948,898 A * | 9/1999 | Dean et al. .................... 536/23.5 |
| 5,955,443 A * | 9/1999 | Bennett et al. ................... 514/44 |
| 6,468,798 B1 * | 10/2002 | Debs et al. ..................... 435/458 |
| 6,582,908 B2 | 6/2003 | Fodor et al. |
| 2004/0013658 A1 * | 1/2004 | Fulton et al. .................. 424/94.1 |

FOREIGN PATENT DOCUMENTS

| | | | |
|---|---|---|---|
| WO | WO 9319203 | 9/1993 | |
| WO | WO 93/24510 | 12/1993 | |
| WO | WO 94/02499 | 2/1994 | |
| WO | WO 94/08003 | 4/1994 | |
| WO | WO 94/17093 | 8/1994 | |
| WO | WO 96/32496 | 10/1996 | |
| WO | WO 96/34008 | 10/1996 | |
| WO | WO 96/40266 | * 12/1996 | |
| WO | WO 98/09633 | * 3/1998 | 536/23.1 |
| WO | WO 99/11778 | 3/1999 | |
| WO | WO 9911778 | 3/1999 | |

OTHER PUBLICATIONS

Yu et al., Hybrid Oligonucleotides: Synthesis, Biophysical Properties, Stability Studies, and Biological Activity, 1996, Bioorganic & Medicinal Chemistry, vol. 4, No. 10, pp. 1685-1692.*

Levesque et al., Antisense Oligonucleotides Targeting Human Protein Kinase C-α Inhibit Phorbol Ester-Induced Reduction of Bradykinin-Evoked Calcium Mobilization in A549 Cells, 1997, Molecular Pharmacology, 51, pp. 209-216.*

Agrawal, S. et al., Ed., *Methods in Molecular Biology*, 1994, 26, Humana Press, Totowa, NJ.

Albert, P.R. et al., "Antisense knockouts: molecular scalpels for the dissection of signal transduction", *Trends Pharmacol. Sci.*, 1994, 15, 250-254.

Allen, L.V., "Inhalation Products", *Secundum Artem (online publication)*. Printed Aug. 11, 1998, 6(3), 11 pages, available at http://www.paddocklabs.com/secundum/secarndx.html.

Alul, R.H. et al., "Oxalyl-CPG: a labile support for synthesis of sensitive oligonucleotide derivatives", *Nuc. Acid Res.*, 1991, 19, 1527-1532.

Ausubel et al. (Eds.), *Short Protocols in Molecular Biology*, 2nd Ed., John Wiley & Sons, New York, NY, Chapter 3, 3-11 to 3-38.

Bailly, C. et al., "PCR-based development of DNA substrates containing modified bases: An efficient system for investigating the role of the exocyclic groups in chemical and structural recognition by minor groove binding drugs and proteins", *Proc. Natl. Acad. Sci. USA.*, 1996, 93, 13623-13628.

Baker et al., "Cleavage of the 5' Cap Structure of mRNA by a Europium (III) Macrocyclic Complex with Pendant Alcohol Groups", *J. Am. Chem. Soc.*, 1997, 119, 8749-8755.

Banchereau et al., "The CD40 Antigen and Its Ligand", *Annu. Rev. Immunol.*, 1994, 12, 881-922.

Beaucage, S.L. et al., "Advances in the Synthesis of Oligonucleotides by the Phosphoramidite Approach", *Tetrahedron*, 1992, 48, 2223-2311.

Beck, S., "Nonradioactive Detection of DNA Using dioxetane Chemiluminescence", *Methods in Enxymology*, 1992, 216, 143-153.

Berge, S.M. et al., "Pharmaceutical Salts", *J. Pharm. Sci.*, 1977, 66, 1-19.

Bochner et al., "Immunological Aspects of Allergic Asthma", *Annu. Rev. Immunol.*, 1994, 12, 295-335.

Brown, T. et al., "Modern machine-aided methods of oligodeoxyribonucleotide synthesis", *Oligonucleotides and Analogs*, 1991, Chapter 1, Ekstein, F., ed., IRL Press, Oxford, 1-24.

Buzayan, J.M. et al., "Satellite tobacco ringspot virus RNA: A subset of the RNA sequence is sufficient for autolytic processing", *Proc. Natl. Acad. Sci. USA*, 1986, 83, 8859-8862.

Cannon et al., "The Flow-Past Chamber: An Improved Nose-Only Exposure System for Rodents", *Amer. Ind. Hyg. Assoc.*, 1983, 44(12), 923-928.

Chen et al., "Deposition of Cigarette Smoke Particles in the Rat", *Fundam. Appl. Toxicol.*, 1989, 13, 429-438.

Chollet, A. et al., "DNA containing the base analogue 2-aminoadenine: preparation, us as hybridization probes and cleavage by restriction endonucleases", *Nucl. Acids Res.*, 1988, 16, 305-317.

Cole-Strauss et al., "Correction of the Mutation Responsible for Sickle Cell Anemia by an RNA-DNA Oligonucleotide", *Science*, 1996, 273, 1386-1389.

Cook, P.D., "Medicinal chemistry of antisense oligonucleotides—future opportunities", *Anti-Cancer Drug Design*, 1991, 6, 585-607.

Crooke, S.T., "Progress in Antisense Therapeutics", *Hematologic Path.*, 1995, 9, 59-72.

Crooke, S.T. et al., "Pharmacokinetic Properties of Several Novel Oligonucleotide Analogs in mice", *J. Pharmacol. Exp. Therapeutics*, 1996, 277, 923-937.

Crooke, S.T. et al., "Progress in the development and patenting of antisense drug discovery technology", *Exp. Opin. Ther. Patents*, 1996, 6, 855-870.

Dean, N.M. et al., "Inhibition of protein kinase C-α expression in mice after systemic administration of phosphorthioate antisense oligodeoxynucleotides", *Proc. Natl. Acad. Sci.*, 1994, 91, 11762-11766.

Delgado, C. et al., "The Uses and Properties of PEG-Linked Proteins", *Crit. Rev. in Therapeutic Drug Carrier Sys.*, 1992, 9, 249-304.

DeLisser et al., "Molecular and functional aspects of PECAM-1/CD31", *Immunol. Today*, 1994, 15, 490-495.

Dosaka-Akita et al., "Inhibition of Proliferation by L-myc Antisense DNA for the Translational Initiation Site in Human Small Cell Lung Cancer", *Cancer Research*, 1995, 55, 1559-1564.

Downward, "The ras superfamily of small GTP-binding proteins", *Trends Biol. Sci.*, 1990, 15, 469-472.

Ellington et al., "In vitro selection of RNA molecules that bind specific ligands", *Nature*, 1990, 346, 818-822.

Englisch, U. et al., "Chemically Modified Oligonucleotides as Probes and Inhibitors", *Angew. Chem. Int. Ed. Eng.*, 1991, 30, 613-629.

Forster, A.C. et al., "Self-Cleavage of Virusoid RNA is Performed by the Proposed 55-Nucleotide Active Site", *Cell*, 1987, 50, 9-16.

Forster et al., "External Guide Sequences for an RNA Enzyme", *Science*, 1990, 249, 783-786.

Gaffney, B.L. et al., The Influence of the Purine 2-Amino Group on DNA Conformation and Stability-II *Tetrahedron*, 1984, 40, 3-13.

Gebeyehu, G. et al., "Novel bitinylated nucleotide—analogs for labeling and colorimetric detection of DNA", *Nucl. Acids Res.*, 1987, 15, 4513-4534.

*Genetic Engineering News*:"ISIS Pharmaceuticals Demonstrates Efficiency in Crohn's Disease with its Antisense Drug", Mar. 1, 1997, pp. 1 and 34.

Georges, R.N. et al., "Prevention of Orthotopic Human Lung Cancer Growth by Intratracheal Instillation of a Retroviral Antisense K-*ras* Construct", *Cancer Res.*, 1993, 53, 1743-1746.

Graham, M.J. et al., "Tritium labeling of antisense oligonucleotides by exchange with tritiated water", *Nucl. Acids Res.*, 1993, 21, 3737-3743.

Greene et al., *Protective Groups in Organic Synthesis*, 1991, Chapter 2, John Wiley & Sons, pp. 11-142.

Greene et al., *Protective Groups in Organic Synthesis*, 1991, Chapter 7, John Wiley & Sons, pp. 309-405.

Greve, J.M. et al., "The Major Human Rhinovirus Receptor is ICAM-1", *Cell*, 1989, 56, 839-847.

Guerrier-Takada et al., "Phenotypic conversion of drug-resistant bacteria to drug sensitivity", *Proc. Natl. Acad. Sci.*, 1997, 94, 8468-8472.

Gundel et al., "Endothelial Leukocyte Adhesion Molecule-1 Mediates Antigen-induced Acute Airway Inflammation and Late-phase Airway Obstruction in Monkeys", *J. Clin. Invest.*, 1991, 88, 1407-1411.

Haseloff et al., "Simple RNA enzymes with new and highly specific endoribonuclease activities", *Nature*, 1988, 334, 585-591.

Hyrup, B. et al., "Peptide Nucleic Acids (PNA): Synthesis, Properties, and Potential Applications", *Biorg. & Med. Chem.*, 1996, 4, 5-23.

Kabanov, A.V., "A new class of antivirals: antisense oligonucleotides combined with a hydrophobic substituent effectively inhibit influenza virus reproduction and synthesis of virus-specific proteins in MDCK cells", *FEBS Letts.*, 1990, 259, 327-330.

Katocs, A.S. et al., "Biological Testing", *Remington's Pharmaceutical Sciences*, 18th Ed., Gennaro (ed.), Mack Publishing Co., Easton, PA, 1990, Ch. 27, 484-494.

Kornberg, A. et al., *DNA Replication*, 1980, W.H. Freeman & Co., San Francisco, 4-7.

Kroschwitz, J.I., "Polynucleotides", *Concise Encyclopedia of Polymer Science and Engineering*, 1990, John Wiley & Sons, New York, 858-859.

Lee, V.H.L. et al., "Mucosal Penetration Enhancers for Facilitation of Peptide and Protein Drug Absorption", *Crit. Rev. Ther. Drug Carrier Systems*, 1991, 8, 91-192.

Letsinger, R.L. et al., "Cholesteryl-conjugated oligonucleotides: Synthesis, properties and activity as inhibitors of replication of human immunodeficiency virus in cell culture", *Proc. Natl. Acad. Sci.*, 1989, 86, 6553-6556.

Litwin et al., "Novel Cytokine-independent Induction of Endothelial Adhesion Molecules Regulated by Platelet/Endothelial Cell Adhesion Molecule (CD31)", *J. Cell Biol.*, 1997, 139, 219-228.

Liu et al., "Costimulation of T-cell growth", *Curr. Opin. Immunol.*, 1992, 4, 265-270.

Manoharan, M. et al., "Lipidic Nucleic Acids", *Tetrahedron Letts.*, 1995, 36, 3651-3654.

Manoharan M. et al., "Cholic Acid-Oligonucliotide Conjugates for Antisense Applications", *Bioorganic Med. Chem. Letts.*, 1994, 4, 1053-1060.

Manoharan, M. et al., "Chemical Modifications to Improve Uptake and Bioavailability of Antisense Oligonucleotides", *Annals NY Acad. Sciences*, 1992, 660, 306-309.

Manoharan, M. et al., "Introduction of a Lipophilic Thioether Tether in the Minor Groove of Nucleic Acids for Antisense Applications", *Bioorg. Med. Chem. Letts.*, 1993, 3, 2765-2770.

Manoharan M. et al.,"Oligonucleotide Conjugates: Alteration of the Pharmacokinetic Properties of Antisense Agents", *Nucleosides and Nucleotides*, 1995, 14, 969-973.

Martin, P., "Ein neuer Zugang zu 2'-O-Alkylribonucleosiden und Eigenschaften deren Oligonucleotide", *Helvetica Chemica Acta*, 1995, 78, 486-504.

Mishra, R.K. et al., "Improved leishmanicidal effect of phosphorotioate antisense oligonucleotides by LDL-medicated delivery", *Biochim. Et Biophysica*, 1995, 1264, 229-237.

Miyao, T. et al., "Stability and Pharmacokinetic Characteristics of Oligonucleotides Modified at Terminal Linkages in Mice", *Antisense Res. & Dev.*, 1995, 5, 115-121.

Muranishi, S., "Absorption Enhancers", *Crit. Rev. Ther. Drug Carrier Systems*, 1990, 7, 1-33.

Newman et al., "Perspectives Series: Cell Adhesion in Vascular Biology", *J. Clin. Invest.*, 1997, 99, 3-7.

Nielsen, P.E. et al., "Sequence-Selective Recognition of DNA by Strand Displacement with a Thymine-Substituted Polyamide", *Science*, 1991, 254, 1497-1500.

Nies, A.S. et al., "Principles of Therapeutics", *Goodman & Gilman's The Pharmacological Basis of Therapeutics*, 9th Ed., Hardman et al. (eds.), McGraw-Hill, New York, NY, 1996, Ch. 3, 43-62.

Nyce, J.W., "Respirable antisense oligonucleotides as novel therapeutic agents for asthma and other pulmonary diseases", *Exp. Opin. Invest. Drugs*, 1997, 6(9), 1149-1156.

Nyce, J.W., et al., "DNA antisense therapy for asthma in an animal model", *Nature*, 1997, 385, 721-725.

Oberhauser, B. et al., "Effective incorporation of 2'-O-methyl-oligonucleotides into liposomes and enhanced cell association through modification with thiocholesterol", *Nucl. Acids Res.*, 1992, 20, 533-538.

Ouchi, T. et al., "Synthesis and Antitumor Activity of Poly(Ethylene Glycol)s Linked to 5'-Fluorouracil via a Urethane or Urea Bond", *Drug Des. & Disc.*, 1992, 9, 93-105.

Phan, S.H., "New strategies for treatment of pulmonary fibrosis", *Thorax.*, 1995, 50, 415-421.

Prosnyak, M.I. et al., "Substitution of 2-Aminoadenine and 5-Methylcytocsine for Adenine and Cytosine in Hybridization Probes Increases the Sensitivity of DNA Fingerprinting", *Genomics*, 1994, 21, 490-494.

Ravasio, N. et al., "Selective Hydrogenations Promoted by Copper Catalysts. 1. Chemoselectivity, Regioselectivity, and Stereoselectivity in the Hydrogenation of 3-Substituted Steroids", *J. Org. Chem.*, 1991, 56, 4329-4333.

Robertson, D., "Chrohn's trial shows the pros of antisense", *Nature Biotech.*, 1997, 15, 209.

Ruth, J.L., "Oligonucleotide-Enzyme Conjugates" *Methods of Molecular Biology*, Agrawal, S. (ed.), Humana Press, Totowa, NJ, 1994, Chapter 6, 167-185.

Saison-Behmoaras, T. et al., "Short modified antisense oligonucleotides directed against Ha-*ras* point mutation induce selective cleavage of the mRNA and inhibit T24 cells proliferation", *EMBO J.*, 1991, 10, 1111-1118.

Sambrook et al. (eds.), "Preparation of Radiolabeled DNA and RNA Probes", *Molecular Cloning: A Laboratory Manual*, 1989, 2d. Ed., Chapter 10, 10.1 to 10.70.

Sanghvi, Y.S. et al., "Oligoribonucleotides", *Antisense Research and Applications*, 1993, CRC Press, Gait, M.J., ed., Chapter 16, pp. 289-301.

Sanghvi, Y.S. et al., "Heterocyclic Base Modifications in Nucleic Acids and Their Applications in Antisense Oligonucleotides", *Antisense Research and Applications*, 1993, CRC Press, Boca Raton, Crooke and Lebleu, eds., Chapter 15, pp. 276-278.

Schreier, H., "Pulmonary (poly)peptide and (poly)nucleic acid delivery", *Adv. Drug. Delivery Reviews*, 1996, 19, 1-2.

Secrist, J.A. et al., "Synthesis and Biological Activity of 4'-Thionucleosides", *10th International Rountable: Nucleosides, Nucleotides and their Biological Applications*, Sep. 16-20, 1992, Abstract 21, Park City, Utah, 40.

Shea, R.G. et al., "Synthesis, hybridization properties and antiviral activity of lipidoligodeoxynucletide conjugates", *Nucl. Acids Res.*, 1990, 18, 3777-3783.

Smith, L.M., "Automated Synthesis and Sequence Analysis", *Analyt. Chem.*, 1988, 60, 381-390.

Staunton, D.E. et al., "A Cell Adhesion Molecule, ICAM-1, is the Major Surface Receptor for Rhinoviruses", *Cell*, 1989, 56, 850-853.

Svinarchuk, F.P. et al., "Inhibition of HIV proliferation in MT-4 cells by antisense oligonucleotide conjugated to lipophilic groups", *Biochimie*, 1993, 79, 49-54.

Stribling, R., et al., "Aerosol gene delivery in vivo", *Proc. Natl Acad. Sci. USA*, 1992, 89, 11277-11281.

Takakura, Y. et al., "Uptake Characteristics of Oligonucleotides in the Isolated Rat Liver Perfusion System", *Antsense & Nuc. Acid Drug Dev.*, 1996, 6, 177-183.

U.S. Congress, Office of Technology Assessment, "The State-of-the-art in Genetic Screening", *Genetic Monitoring and Screening in the Workplace*, OTA-BA-455, U.S. Government Printing Office, Washington, D.C., 1990, Ch. 5, 75-99.

Wahlestedt, C. et al., "Modulation of Anxiety and Neuropeptide Y-Y1 Recptors by Antisense Oligodeoxynucleotides", *Science*, 1993, 259, 528-531.

Wahlestedt, C. et al., "Antisense oligodeoxynucleotides to NMDA-R1 receptor channel protect cortical neurons from excitotoxicity and reduce focal ischaemic infarctions", *Nature*, 1993, 363, 260-263.

Warren et al., "Protocols for Oligonucleotides Conjugates", *Methods in Molecular Biology*, Agrawal, S. (ed.), Humana Press, Totowa, NJ, 1994, vol. 26, Chapter 9, 233-264.

Wegner et al., "Intercellular Adhesion Molecule-1 (ICAM-1) in Pathogenesis of Asthma", *Science*, 1994, 247, 456-459.

Wright, P. et al., "Large Scale Synthesis of Oligonucleotides via phosphoramidite Nucleosides and a High-loaded Polystyrene Support", *Tetrahedron Letts.*, 1993, 34, 3373-3376.

Wu-Pong, S. et al., "Airway-to-biophase transfer of inhaled oligonucleotides", *Adv. Drug Deliv. Rev.*, 1996, 19, 47-71.

Yoshimura, K., "Expression of the human cystic fibrosis transmembrane conductance regulator gene in the mouse lung after in vivo intratracheal plasmid-mediated gene transfer", *Nucl. Acids Res.*, 1992, 20, 3233-3240.

U.S. Appl. No. 08/383,666, filed Feb. 3, 1995, Cook et al.
U.S. Appl. No. 08/398,901, filed Mar. 6, 1995, Cook et al.
U.S. Appl. No. 08/465,880, filed Jun. 6, 1995, Cook et al.
U.S. Appl. No. 08/468,037, filed Jun. 6, 1995, Cook et al.
U.S. Appl. No. 08/762,488, filed Dec. 10, 1996.
U.S. Appl. No. 08/777,266, filed Dec. 31, 1996, Bennett et al.
U.S. Appl. No. 09/009,490, filed Jan. 20, 1998, Bennett et al.
U.S. Appl. No. 09/016,520, filed Jan. 30, 1998.
U.S. Appl. No. 09/044,506, filed Mar. 19, 1998, Bennett et al.
U.S. Appl. No. 09/062,416, filed Apr. 17, 1998, Bennett et al.
U.S. Appl. No. 09/071,433, filed May 1, 1998, Bennett et al.
The EPO Supplementary Partial European Search Report dated Jul. 16, 2003 (EP 99 92 3251).

Levesque, L., et al., "Antisense oligonucleotides targeting human protein kinase C-α inhibit phorbol ester-induced reduction of bradykinin-evoked calcium mobilization in A549 cells," *Molecular Pharm.*, XP-002247729, 1997, 51, 209-216.

McKay, R.A., "Characterization of a potent and specific class of antisense oligonucleotide inhibitor of human protein kinase C-α expression," *J. of Biological Chem.*, XP-002247728, Jan. 15, 1999, 274(3), 1715-1722.

Nicklin, P.L., et al., "Pulmonary bioavailability of a phosphorothioate oligonucleotide (CGP 64128A): comparison with other delivery routes," *Pharm. Res.*, XP008019675, 1998, 15(4), 583-591.

Nyce, J.W., "Respirable antisense oligonucleotides as novel therapeutic agents for asthma and other pulmonary diseases," *Exp. Opin. Invest. Drugs*, XP002919983, 1997, 6(9), 1149-1156.

Rojanasakul, Y., et al., "Antisense inhibition of silica-induced tumor necrosis factor in alveolar macrophages," XP-002247730, Feb. 14, 1997, 272(7), 3910-3914.

Schreier, H., "Pulmonary (poly)peptide and (poly)nucleic acid delivery," *Advanced Drug Delivery Rev.*, XP002919984, 1996, 19, 1-2.

Wu-Pong, S., et al., "Airway-to-biophase transfer of inhaled oligonucleotides," *Advanced Drug Delivery Rev.*, XP002919982, 1996, 19, 47-71.

Branch et al., "A good antisense molecule is hard to find," TIBS (1998) 23:45-50.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

International Search Report for Application # PCT/US99/11141 (ISIS-3562) dated Aug. 5, 1999.

New England Biolabs 1998/99 Catalog (cover page and pp. 121 and 284).

Reynolds et al., "Rational siRNA design for RNA interference" Nature Biotechnology (2004) 22(3):326-330.

* cited by examiner

Figure 2. Lung Pharmacokinetics Following Inhalation Exposure of ISIS 2105 to Mice

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Antisense sequence

<400> SEQUENCE: 1
gcccaagctg gcatccgtca                                              20

<210> SEQ ID NO 2
<211> LENGTH: 21
<212> TYPE: DNA
<213> ORGANISM: Artificial Sequence
<220> FEATURE:
<223> OTHER INFORMATION: Antisense sequence

<400> SEQUENCE: 2
gcgtttgctc ttcttcttgc g                                            21

<210> SEQ ID NO 3
<211> LENGTH: 20
<212> TYPE: DNA
<213> ORGANISM: Artificial Sequence
<220> FEATURE:
<223> OTHER INFORMATION: Antisense sequence

<400> SEQUENCE: 3
gttctcgctg gtgagtttca                                              20

<210> SEQ ID NO 4
<211> LENGTH: 15
<212> TYPE: DNA
<213> ORGANISM: Artificial Sequence
<220> FEATURE:
<223> OTHER INFORMATION: Antisense sequence

<400> SEQUENCE: 4
aacttgtgct tgctc                                                   15

<210> SEQ ID NO 5
<211> LENGTH: 20
<212> TYPE: DNA
<213> ORGANISM: Artificial Sequence
<220> FEATURE:
<223> OTHER INFORMATION: Antisense sequence

<400> SEQUENCE: 5
gccaaggagt ttgagatagt                                              20

<210> SEQ ID NO 6
<211> LENGTH: 20
<212> TYPE: DNA
<213> ORGANISM: Artificial Sequence
<220> FEATURE:
<223> OTHER INFORMATION: Antisense sequence
```

```
<400> SEQUENCE: 6
ccgcagccat gcgctcttgg                                                       20

<210> SEQ ID NO 7
<211> LENGTH: 20
<212> TYPE: DNA
<213> ORGANISM: Artificial Sequence
<220> FEATURE:
<223> OTHER INFORMATION: Antisense sequence

<400> SEQUENCE: 7
gtgtgccaga caccctatct                                                       20

<210> SEQ ID NO 8
<211> LENGTH: 20
<212> TYPE: DNA
<213> ORGANISM: Artificial Sequence
<220> FEATURE:
<223> OTHER INFORMATION: Antisense sequence

<400> SEQUENCE: 8
gctgattaga gagaggtccc                                                       20

<210> SEQ ID NO 9
<211> LENGTH: 20
<212> TYPE: DNA
<213> ORGANISM: Artificial Sequence
<220> FEATURE:
<223> OTHER INFORMATION: Antisense sequence

<400> SEQUENCE: 9
ttgcttccat cttcctcgtc                                                       20

<210> SEQ ID NO 10
<211> LENGTH: 20
<212> TYPE: DNA
<213> ORGANISM: Artificial Sequence
<220> FEATURE:
<223> OTHER INFORMATION: Antisense sequence

<400> SEQUENCE: 10
ggagtccagc actagcactg                                                       20
```

COMPOSITION AND METHODS FOR THE PULMONARY DELIVERY OF NUCLEIC ACIDS

CROSS REFERENCE TO RELATED APPLICATIONS

This application is a continuation-in-part of Ser. No. 09/083,586, filed May 21, 1998 (abandoned), the disclosure of which is incorporated by reference herein in its entirety.

FIELD OF THE INVENTION

The present invention relates to compositions and methods for the delivery of nucleic acid therapeutics and diagnostics to the lung of an animal, particularly a human. More particularly, the present invention is directed to compositions and methods for the pulmonary delivery of oligonucleotide therapeutics and diagnostics, including antisense oligonucleotides. In some preferred embodiments, the present invention is directed to methods and compositions for pulmonary delivery of oligonucleotide therapeutic compositions comprising penetration enhancers, carrier compounds and/or transfection agents.

More specific objectives and advantages of the invention will hereinafter be made clear or become apparent to those skilled in the art during the course of explanation of preferred embodiments of the invention.

BACKGROUND OF THE INVENTION

Advances in the field of biotechnology have given rise to significant advances in the treatment of previously-intractable diseases such as cancer, genetic diseases, arthritis and AIDS. Many such advances involve the administration of oligonucleotides and other nucleic acids to a subject, particularly a human subject.

Oligonucleotides have been administered by various routes. For example, oligonucleotides administered by parenteral routes have been shown to be effective for the treatment of diseases and/or disorders. See, e.g., U.S. Pat. No. 5,595,978, Jan. 21, 1997 to Draper et al., which discloses intravitreal injection as a means for the direct delivery of antisense oligonucleotides to the vitreous humor of the mammalian eye. See also, Robertson, *Nature Biotechnology*, 1997, 15:209 and Anon., *Genetic Engineering News*, 1997, 15:1, each of which discuss the treatment of Crohn's disease via intravenous infusions of antisense oligonucleotides.

The administration of oligonucleotides via the lung for the treatment of pulmonary disorders is attractive because oligonucleotide is delivered directly to the target organ. For reviews see, for example, Nyce, J. W., *Exp. Opin. Invest. Drugs* (1997) 6(9):1149-1156; Schreier, H., *Advanced Drug Delivery Reviews*, 19, (1996) 1-2; Wu-Pong, S., and Byron, P. R., *Advanced Drug Delivery Reviews*, 19, (1996) 47-71; and Phan, S. H., *Thorax* 1995; 50: 415-421. However, most reports have focused upon intratracheal rather than inhalation delivery of large nucleic acids that are antisense constructs rather than of antisense oligonucleotides having smaller molecular weights. See, for example, Georges, R. N., et al., *Cancer Research* 53, 1743-1746 (1993) (prevention of orthotopic human lung cancer growth by intratracheal installation of a retroviral antisense K-ras construct); and Yoshimura, K., et al., *Nucleic Acids Research*, Vol. 20, No. 12, 3233-3240 (1992) (expression of the human cystic fibrosis transmembrane conductance regulator gene in the mouse lung after in vivo intratracheal plasmid-mediated gene transfer).

Antisense oligonucleotides have been shown to demonstrate antisense effect upon cells of various diseases or disorders, including cancer. See, for example, Dosaka-Akita et al., Cancer Res. 55, 1559-1564 (1995) (inhibition of proliferation by L-myc antisense DNA for the transitional initiation site in human small cell lung cancer).

There is a long-felt need for compositions which can effectively provide for the pulmonary delivery of nucleic acids, particularly oligonucleotides, more particularly oligonucleotides having one or more chemical modifications, together with methods for using such compositions to deliver such oligonucleotides and nucleic acids into the lung of an animal. The present invention is directed to these, as well as other, important ends.

SUMMARY OF THE INVENTION

The present invention is directed to compositions and methods for pulmonary delivery of oligonucleotides.

In some preferred embodiments, the present invention provides pharmaceutical compositions for pulmonary delivery of an oligonucleotide comprising at least one oligonucleotide wherein the sugar moiety of at least one nucleoside unit of said oligonucleotide is not a 2'-deoxyribofuranosyl sugar moiety or at least one internucleotide linkage within said oligonucleotide is not a phosphodiester or a phosphorothioate linkage.

Also provided in accordance with the present invention are methods for the administration of an nucleic acid therapeutic or diagnostic composition comprising:

preparing a nucleic acid therapeutic or diagnostic composition;

aerosolizing the nucleic acid composition; introducing the aerosolized nucleic acid composition into the lung of a mammal; and wherein the aerosolized nucleic acid composition comprises at least one oligonucleotide wherein the sugar moiety of at least one nucleoside unit of said oligonucleotide is not a 2'-deoxyribofuranosyl sugar moiety or at least one internucleotide linkage within said oligonucleotide is not a phosphodiester or a phosphorothioate linkage.

The present invention also provides methods of treating an animal having or suspected of having a disease or disorder that is treatable with one or more nucleic acids comprising administering a therapeutically effective amount of an aerosolized nucleic acid composition to the lung of the animal, wherein the aerosolized nucleic acid composition comprises at least one oligonucleotide wherein the sugar moiety of at least one nucleoside unit of said oligonucleotide is not a 2'-deoxyribofuranosyl sugar moiety or at least one internucleotide linkage within said oligonucleotide is not a phosphodiester or a phosphorothioate linkage.

Also provided by the present invention are methods of investigating the role of gene or gene product in an animal other than a human comprising administering a therapeutically effective amount of an aerosolized nucleic acid composition to the lung of the animal, wherein the aerosolized nucleic acid composition comprises at least one oligonucleotide wherein the sugar moiety of at least one nucleoside unit of said oligonucleotide is not a 2'-deoxyribofuranosyl sugar moiety or at least one internucleotide linkage within said oligonucleotide is not a phosphodiester or a phosphorothioate linkage.

In some preferred embodiments, methods are provided for delivering an oligonucleotide therapeutic or diagnostic compound to the lung of an animal comprising applying to said lung a pharmaceutical composition according to the invention.

Preferably, the oligonucleotide is delivered within cells of said lung. In some preferred embodiments, the methods of the invention are performed on an animal that is known or suspected to suffer from a disease or disorder.

In some preferred embodiments, the sugar moiety of at least one nucleoside unit of said oligonucleotide is not a 2'-deoxyribofuranosyl sugar moiety.

In further preferred embodiments, said nucleoside unit is a 2'-O-substituted nucleoside unit.

In some particularly preferred embodiments, said 2-O-substituent of said 2'-O-substituted nucleoside unit is a 2'-O-alkoxyalkoxy substituent.

In some particularly preferred embodiments, said 2-O-substituent of said 2'-O-substituted nucleoside unit is a 2'-O-dialkylaminooxyalkyl substituent.

In some preferred embodiments, at least one internucleotide linkage within said oligonucleotide is not a phosphodiester or a phosphorothioate linkage.

In further preferred embodiments, at least one internucleotide linkage within said oligonucleotide is a 3'-methylene-phosphonate, a non-phosphorus containing oligonucleoside linkage, a 2'-5' linkage or is a 3'-deoxy-3'-amino phosphoramide linkage.

In some preferred embodiments, the compositions further comprise one or more pharmaceutically acceptable carriers.

In some preferred embodiments, said composition is in aqueous media. In other preferred embodiments, said aqueous media is sterilized, pyrogen free water. In further preferred embodiments, said aqueous media is saline solution. In still further preferred embodiments, the pharmaceutical composition is a powder.

Preferably, the compositions of the invention comprise an oligonucleotide that is an antisense oligonucleotide.

In some preferred embodiments, said antisense compound modulates the expression of a protein or modulates a rate of cellular proliferation. In further preferred embodiments, said antisense oligonucleotide modulates expression of a cellular adhesion protein.

In still further preferred embodiments, the antisense oligonucleotide is antisense to a genetic sequence implicated in a disease or disorder, preferably, asthma, a cancer of the lung, pulmonary fibrosis, rhinovirus, tuberculosis, bronchitis, or pneumonia.

In some preferred embodiments, said antisense oligonucleotide is antisense to a portion of a gene coding for a cytokine. In further preferred embodiments, said antisense oligonucleotide is antisense to a portion of a gene coding for ICAM-1, ELAM-1, VCAM-1, B7-1, B7-2, CD40, LFA-3, PECAM-1, a ras oncogene, an H-ras oncogene, a K-ras oncogene, Protein Kinase C, or to a unique portion of the genome of *Mycobacterium tuberculosis, M. bovis*, or *Streptococcus pneumoniae.*

In some preferred embodiments, the pharmaceutical compositions of the invention comprise more than one antisense oligonucleotide.

In further preferred embodiments, the oligonucleotide is a ribozyme, an external guide sequence, or an antisense peptide nucleic acid.

In further preferred embodiments, said oligonucleotide is an aptamer or a molecular decoy.

In further preferred embodiments, said aqueous media is sterilized, pyrogen free buffer solution.

In some preferred embodiments, the nucleic acid therapeutic composition is an aerosolized solution that consists essentially of an antisense oligonucleotide in saline solution.

In other preferred embodiments, the nucleic acid therapeutic composition is an aerosolized solution that consists essentially of an antisense oligonucleotide in buffer solution.

The present invention also provides methods of modulating the expression of a gene in an animal comprising administering to said animal the pharmaceutical composition of the invention.

The present invention also provides medical devices for pulmonary delivery of an aerosol comprising a pharmaceutical composition in accordance with the present invention. Preferably, the medical device is a nebulizer.

In a further aspect, the present invention provides novel compounds comprising at least one moiety of Formula:

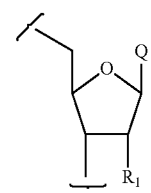

wherein:

$R_1$ has the formula —O—$R_5$—O—$R_6$;

$R_5$ and $R_6$ are independently alkyl having from 1 to about five carbons; and Q is 5-methylcytosine.

In especially preferred embodiments, $R_5$ is —$CH_2$—$CH_2$—$CH_2$— and $R_6$ is —$CH_3$.

In further preferred embodiments, compounds are provided having the formula:

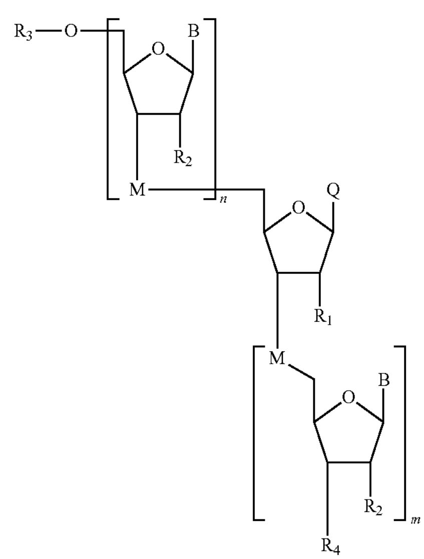

wherein:

$R_1$ has the formula —O—$R_5$—O—$R_6$;

$R_5$ and $R_6$ are independently alkyl having from 1 to about five carbons;

Q is 5-methylcytosine;

M is an internucleoside linkage;

B is a nucleobase;

each $R_2$ is H, OH, F, or a group of formula $R_7$—$(R_8)_v$;

$R_7$ is $C_3$-$C_{20}$alkyl, $C_4$-$C_{20}$alkenyl, $C_2$-$C_{20}$alkynyl, $C_1$-$C_{20}$alkoxy, $C_2$-$C_{20}$alkenyloxy, or $C_2$-$C_{20}$alkynyloxy;

$R_8$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides;

$R_3$ is H or a hydroxyl protecting group;

$R_4$ is H, OH, an internucleoside linkage, a linker connected to a solid support, or a group of formula —O—Pr where Pr is a hydroxyl protecting group; and m and n are each independently from 0 to about 50.

In some preferred embodiments, $R_5$ is —$CH_2$—$CH_2$— and $R_6$ is —$CH_3$. In further preferred embodiments, each $R_1$ is —O—$CH_2$—$CH_2$—O—$CH_3$.

In some especially preferred embodiments, each $R_2$ is —O—$CH_2$—$CH_2$—O—$CH_3$, and B is selected from the group consisting of 5-methylcytosine, adenine, guanine, uracil and thymine.

In particularly preferred embodiments, oligonucleotides are provided comprising one or more 5-methylcytosine-2'-methoxyethoxy nucleosidic moieties.

In further particularly preferred embodiments, pharmaceutical compositions are provided comprising a compound of the invention.

BRIEF DESCRIPTION OF THE DRAWINGS

The numerous objects and advantages of the present invention may be better understood by those skilled in the art by reference to the accompanying figures, in which:

FIG. 2 shows nebulization of oligonucleotide (ISIS 2503; 40 mg/mL) by a PulmoAide Nebulizer (Apguard Medical, Inc., Woodland Hills, Calif.) for a period of 20 minutes. The mist coming out of the nebulizer was collected in an impinger and was analyzed for oligonucleotide content by ultraviolet absorption. The straight line of the graph indicates that the nebulization was uniform over the course of the experiment.

DETAILED DESCRIPTION OF PREFERRED EMBODIMENTS

The present invention provides compositions and methods for the pulmonary delivery of oligonucleotides and other nucleic acids to the lung of an animal. In preferred embodiments, the present invention provides compositions and methods for modulating the in vivo expression of a gene in an animal through the pulmonary administration of an antisense oligonucleotide, thereby bypassing the complications and expense which may be associated with intravenous and other routes of administration. Enhanced delivery of the oligonucleotides and other nucleic acids to the lung of an animal is achieved through the use of the compositions and methods of the invention.

Studies suggest that oligonucleotides are rapidly eliminated from plasma and accumulate mainly in the liver and kidney after i.v. administration (Miyao et al., *Antisense Res. Dev.,* 1995, 5:115; Takakura et al., *Antisense & Nucl. Acid Drug Dev.,* 1996, 6:177). Means for measuring and avoiding "first pass clearance" effects are needed for the development of effective agents to treat diseases or disorders of the lung.

One means of ameliorating first pass clearance effects is to increase the dose of an administered drug, thereby compensating for proportion of drug lost to first pass clearance. Although this may be readily achieved with i.v. administration by, for example, simply providing more of the drug to an animal, other factors influence the bioavailability of administered drugs.

The present invention provides compositions for the pulmonary administration of oligonucleotides that can contain carrier compounds, penetration enhancing agents, and transfection agents. However, the present invention also provides compositions and methods for the pulmonary administration of oligonucleotides that are substantially free of As used herein, the term "substantially free of carriers or penetration enhancing agents" means that a de minimis amount (i.e., an amount less than that recognized to be effective) of carriers or penetration enhancing agents can be present in the composition. In particular, these modalities of the invention are drawn to compositions that comprise less than 10 mole percent, preferably less than 1 mole percent and most preferably less than 0.1 mole percent of such carriers or penetration enhancing agents.

In some preferred embodiments, the present invention provides pharmaceutical compositions for pulmonary administration of large molecule therapeutics such as oligonucleotides comprising the oligonucleotide and at least one substance which facilitates the transport of a drug across the mucous membrane(s) of the lung (so called "mucosal penetration enhancers," also known as "absorption enhancers" or simply as "penetration enhancers"). See Muranishi, *Crit. Rev. Ther. Drug Carrier Systems,* 1990, 7:1 and Lee et al., *Crit. Rev. Ther. Drug Carrier Systems,* 1991, 8:91.

The present invention provides compositions and methods for pulmonary delivery of one or more nucleic acids to an animal. For purposes of the invention, the term "animal" is meant to encompass humans as well as other mammals, as well as reptiles, fish, amphibians, and birds. The term "pulmonary delivery" refers to the administration, directly or otherwise, to a portion of the lung of an animal. The term "lung" has its accustomed meaning as the chief organ of respiration (i.e. gas exchange) in an animal. As used herein, the term "pulmonary delivery" subsumes the absorption of the delivered component from the interior surface of lung, into the lung tissue.

The present invention provides compositions and methods for the pulmonary administration of oligonucleotides. The compositions can contain carrier compounds, penetration enhancing agents, and/or transfection agents. As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioated oligonucleotide in hepatic tissue is reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5:115; Takakura et al., *Antisense & Nucl. Acid Drug Dev.*, 1996, 6:177).

Figure 1:
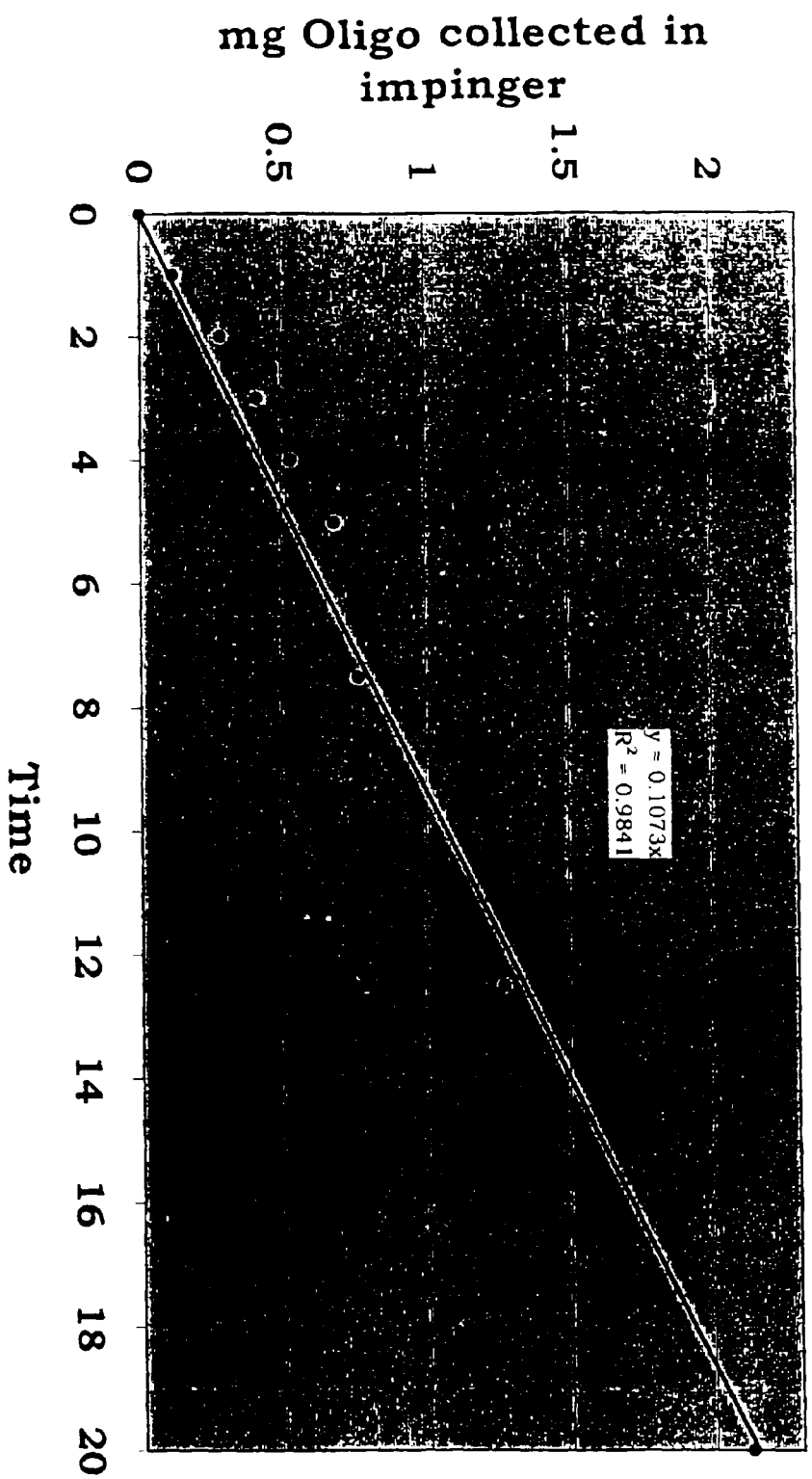
FIG. 1 is a plot showing that oligonucleotides were uniformly nebulized, and that the size of the resultant particles is not altered over time.

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.).

In some preferred embodiments, the present invention employs oligonucleotides for use in antisense modulation of the function of DNA or messenger RNA (mRNA) encoding a protein the modulation of which is desired, and ultimately to regulate the amount of such a protein. Hybridization of an antisense oligonucleotide with its mRNA target interferes with the normal role of mRNA and causes a modulation of its function in cells. The functions of mRNA to be interfered with include all vital functions such as translocation of the RNA to the site for protein translation, actual translation of protein from the RNA, splicing of the RNA to yield one or more mRNA species, turnover or degradation of the mRNA and possibly even independent catalytic activity which may be engaged in by the RNA. The overall effect of such interference with mRNA function is modulation of the expression of a protein, wherein "modulation" means either an increase (stimulation) or a decrease (inhibition) in the expression of the protein. In the context of the present invention, inhibition is the preferred form of modulation of gene expression.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

An oligonucleotide is a polymer of repeating units generically known as a nucleotides. An unmodified (naturally occurring) nucleotide has three components: (1) a nitrogenous base linked by one of its nitrogen atoms to (2) a 5-carbon cyclic sugar and (3) a phosphate, esterified to carbon 5 of the sugar. When incorporated into an oligonucleotide chain, the phosphate of a first nucleotide is also esterified to carbon 3 of the sugar of a second, adjacent nucleotide. The "backbone" of an unmodified oligonucleotide consists of (2) and (3), that is, sugars linked together by phosphodiester linkages between the carbon 5 (5') position of the sugar of a first nucleotide and the carbon 3 (3') position of a second, adjacent nucleotide. A "nucleoside" is the combination of (1) a nucleobase and (2) a sugar in the absence of (3) a phosphate moiety (Kornberg, A., *DNA Replication*, W.H. Freeman & Co., San Francisco, 1980, pages 4-7). The backbone of an oligonucleotide positions a series of bases in a specific order; the written representation of this series of bases, which is conventionally written in 5' to 3' order, is known as a nucleotide sequence.

Oligonucleotides may comprise nucleotide sequences sufficient in identity and number to effect specific hybridization with a particular nucleic acid. Such oligonucleotides which specifically hybridize to a portion of the sense strand of a gene are commonly described as "antisense." In the context of the invention, "hybridization" means hydrogen bonding, which may be Watson-Crick, Hoogsteen or reversed Hoogsteen hydrogen bonding, between complementary nucleotides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA to cause a decrease or loss of function, and there is a sufficient degree of complementarity to avoid non-specific binding of the oligonucleotide to non-target sequences under conditions in which specific binding is desired, i.e., under physiological conditions in the case of in vivo assays or therapeutic treatment, or in the case of in vitro assays, under conditions in which the assays are performed.

Antisense oligonucleotides are commonly used as research reagents, diagnostic aids, and therapeutic agents. For example, antisense oligonucleotides, which are able to inhibit gene expression with exquisite specificity, are often used by those of ordinary skill to elucidate the function of particular genes, for example to distinguish between the functions of various members of a biological pathway. This specific inhibitory effect has, therefore, been harnessed by those skilled in the art for research uses. The specificity and sensitivity of oligonucleotides is also harnessed by those of skill in the art for therapeutic uses. For example, the following U.S. patents demonstrate palliative, therapeutic and other methods utilizing antisense oligonucleotides. U.S. Pat. No. 5,135,917 provides antisense oligonucleotides that inhibit human interleukin-1 receptor expression. U.S. Pat. No. 5,098,890 is directed to antisense oligonucleotides complementary to the c-myb oncogene and antisense oligonucleotide therapies for certain cancerous conditions. U.S. Pat. No. 5,087,617 provides methods for treating cancer patients with antisense oligonucleotides. U.S. Pat. No. 5,166,195 provides oligonucleotide inhibitors of Human Immunodeficiency Virus (HIV). U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenzavirus. U.S. Pat. No. 4,806,463 provides antisense oligonucleotides and methods using them to inhibit HTLV-III replication. U.S. Pat. No. 5,286,717 provides oligonucleotides having a complementary base sequence to a portion of an oncogene. U.S. Pat. No. 5,276,019 and U.S. Pat. No. 5,264,423 are directed to phosphorothioate oligonucleotide analogs used to prevent replication of foreign nucleic acids in cells. U.S. Pat. No. 4,689,320 is directed to antisense oligonucleotides as antiviral agents specific to cytomegalovirus (CMV). U.S. Pat. No. 5,098,890 provides oligonucleotides complementary to at least a portion of the mRNA transcript of the human c-myb gene. U.S. Pat. No. 5,242,906 provides antisense oligonucleotides useful in the treatment of latent Epstein-Barr virus (EBV) infections. Other examples of antisense oligonucleotides are provided herein.

The oligonucleotides in accordance with this invention preferably comprise from about 8 to about 30 nucleotides. It is more preferred that such oligonucleotides comprise from about 15 to 25 nucleotides. As is known in the art, a nucleotide is a base-sugar combination suitably bound to an adjacent nucleotide through a phosphodiester, phosphorothioate or other covalent linkage. In the context of this invention, the term "oligonucleotide" includes oligonucleotides composed of naturally-occurring nucleobases, sugars and covalent intersugar (backbone) linkages as well as oligonucleotides having non-naturally-occurring portions which function similarly. Such modified or substituted oligonucleotides may be preferred over native forms because of desirable properties such as, for example, enhanced cellular uptake, enhanced binding to target and increased stability in the presence of nucleases.

Oligonucleotides are also useful in determining the nature, function and potential relationship to body or disease states in animals of various genetic components of the body. Heretofore, the function of a gene has been chiefly examined by the construction of loss-of-function mutations in the gene (i.e., "knock-out" mutations) in an animal (e.g., a transgenic mouse). Such tasks are difficult, time-consuming and cannot be accomplished for genes essential to animal development since the "knock-out" mutation would produce a lethal phenotype. Moreover, the loss-of-function phenotype cannot be transiently introduced during a particular part of the animal's life cycle or disease state; the "knock-out" mutation is always present. "Antisense knockouts," that is, the selective modulation of expression of a gene by antisense oligonucleotides, rather than by direct genetic manipulation, overcomes these limitations (see, for example, Albert et al., *Trends in Pharmacological Sciences*, 1994, 15:250). In addition, some genes produce a variety of mRNA transcripts as a result of processes such as alternative splicing; a "knock-out" mutation typically removes all forms of mRNA transcripts produced from such genes and thus cannot be used to examine the biological role of a particular mRNA transcript. By providing compositions and methods for the simple alimentary delivery of oligonucleotides and other nucleic acids, the present invention overcomes these and other shortcomings.

The present invention further encompasses compositions employing ribozymes. Synthetic RNA molecules and derivatives thereof that catalyze highly specific endoribonuclease activities are known as ribozymes. (See, generally, U.S. Pat. No. 5,543,508 to Haseloff et al., issued Aug. 6, 1996, and U.S. Pat. No. 5,545,729 to Goodchild et al., issued Aug. 13, 1996.) The cleavage reactions are catalyzed by the RNA molecules themselves. In naturally occurring RNA molecules, the sites of self-catalyzed cleavage are located within highly conserved regions of RNA secondary structure (Buzayan et al., *Proc. Natl. Acad. Sci. U.S.A.*, 1986, 83, 8859; Forster et al., *Cell*, 1987, 50, 9). Naturally occurring autocatalytic RNA molecules have been modified to generate ribozymes which can be targeted to a particular cellular or pathogenic RNA molecule with a high degree of specificity. Thus, ribozymes serve the same general purpose as antisense oligonucleotides (i.e., modulation of expression of a specific gene) and, like oligonucleotides, are nucleic acids possessing significant portions of single-strandedness. That is, ribozymes have substantial chemical and functional identity with oligonucleotides and are thus considered to be equivalents for purposes of the present invention.

Other biologically active oligonucleotides may be formulated in the compositions of the invention and used for therapeutic, palliative or prophylactic purposes according to the methods of the invention. Such other biologically active oligonucleotides include, but are not limited to, antisense compounds including, inter alia, antisense oligonucleotides, antisense PNAs and ribozymes (described supra) and EGSs, as well as aptamers and molecular decoys (described infra).

Sequences that recruit RNase P are known as External Guide Sequences, hence the abbreviation "EGS." EGSs are antisense compounds that direct of an endogenous nuclease (RNase P) to a targeted nucleic acid (Forster et al., *Science*, 1990, 249, 783; Guerrier-Takada et al., *Proc. Natl. Acad. Sci. USA*, 1997, 94, 8468).

Antisense compounds may alternatively or additionally comprise a synthetic moiety having nuclease activity covalently linked to an oligonucleotide having an antisense sequence instead of relying upon recruitment of an endogenous nuclease. Synthetic moieties having nuclease activity include, but are not limited to, enzymatic RNAs (as in ribozymes), lanthanide ion complexes, and the like (Haseloff et al., *Nature*, 1988, 334, 585; Baker et al., *J. Am. Chem. Soc.*, 1997, 119, 8749).

Aptamers are single-stranded oligonucleotides that bind specific ligands via a mechanism other than Watson-Crick base pairing. Aptamers are typically targeted to, e.g., a protein and are not designed to bind to a nucleic acid (Ellington et al., *Nature*, 1990, 346, 818).

Molecular decoys are short double-stranded nucleic acids (including single-stranded nucleic acids designed to "fold back" on themselves) that mimic a site on a nucleic acid to which a factor, such as a protein, binds. Such decoys are expected to competitively inhibit the factor; that is, because the factor molecules are bound to an excess of the decoy, the concentration of factor bound to the cellular site corresponding to the decoy decreases, with resulting therapeutic, palliative or prophylactic effects. Methods of identifying and constructing nucleic acid decoy molecules are described in, e.g., U.S. Pat. No. 5,716,780 to Edwards et al.

Another type of bioactive oligonucleotide is an RNA-DNA hybrid molecule that can direct gene conversion of an endogenous nucleic acid (Cole-Strauss et al., *Science*, 1996, 273, 1386).

It has been discovered in accordance with the present invention that pulmonary administration of phosphodiester oligonucleotides is particularly advantageous. Specifically, it has been discovered in accordance with the present invention that the level of nuclease activity in lung tissue is sufficiently low to afford phosphodiester oligonucleotides longer lifetimes in lung tissue than was previously believed. Accordingly, contrary to conventional knowledge in the art (see, e.g., Wu-Pong et al., *Adv. Drug Delivery*, 1996, 19, 47), phosphodiester antisense oligonucleotides reside undegraded in the lung for a sufficiently long period of time to exert an antisense effect.

In further preferred embodiments, the present invention provides oligonucleotides, preferably phosphodiester and phosphorothioate oligonucleotides, that have at least one 2'-alkoxy-alkyloxy substituent, which is preferably, 2'-methoxyethoxy. It has been discovered that the presence of such 2'-alkoxy-alkyloxy substituents confer nuclease resistance, and increased binding. A further preferred modification includes 2'-dimethylaminooxyethoxy, i.e., a O(CH$_2$)$_2$ON (CH$_3$)$_2$ group, also known as 2'-DMAOE, as described in co-owned U.S. patent application Ser. No. 09/016,520, filed on Jan. 30, 1998, the contents of which are herein incorporated by reference. Other preferred modifications include 2'-methoxy (2'-O—CH$_2$), 2'-aminopropoxy (2'-OCH$_2$CH$_2$CH$_2$NH$_2$) and 2'-fluoro (2'-F).

Other specific oligonucleotide chemical modifications are described in the following subsections. It is not necessary for all positions in a given compound to be uniformly modified, and in fact more than one of the following modifications may be incorporated in a single antisense compound or even in a single residue thereof, for example, at a single nucleoside within an oligonucleotide.

Base Modifications For each nucleoside of an oligonucleotide, the base portion of the nucleoside may be selected from a large palette of different base units available. These may be 'modified' or 'natural' bases (also reference herein as nucleobases) including the natural purine bases adenine (A) and guanine (G), and the natural pyrimidine bases thymine (T), cytosine (C) and uracil (U). They further can include modified nucleobases including other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo uracils and cytosines particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering*, pages 858-859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2 C (Sanghvi, Y. S., Crooke, S. T. and Lebleu, B., eds., *Antisense Research and Applications*, CRC Press, Boca Raton, 1993, pp. 276-278) and are presently preferred for selection as the base. These are particularly useful when combined with a 2'-methoxyethyl sugar modifications, described below.

Further representative nucleobases include adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally and non naturally occurring nucleobases include those disclosed in U.S. Pat. No. 3,687,808 (Merigan, et al.), in chapter 15 by Sanghvi, in *Antisense Research and Application*, Ed. S. T. Crooke and B. Lebleu, CRC Press, 1993, in Englisch et al., *Angewandte Chemie, International Edition*, 1991, 30, 613-722 (see especially pages 622 and 623, and in the *Concise Encyclopedia of Polymer Science and Engineering*, J. I. Kroschwitz Ed., John Wiley & Sons, 1990, pages 858-859, Cook, P. D., *Anti-Cancer Drug Design*, 1991, 6, 585-607, each of which are hereby incorporated by reference in their entirety. The term 'nucleosidic base' is further intended to include heterocyclic compounds that can serve as like nucleosidic bases including certain 'universal bases' that are not nucleosidic bases in the most classical sense but serve as nucleosidic bases. Especially mentioned as a universal base is 3-nitropyrrole.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, Reference is also made to allowed U.S. patent application Ser. No. 08/762,588, filed on Dec. 10, 1996, commonly owned with the present application and herein incorporated by reference.

In selecting the base for any particular nucleoside of an oligonucleotide, consideration is first given to the need of a base for a particular specificity for hybridization to an opposing strand of a particular target. Thus if an 'A' base is required, adenine might be selected however other alternative bases that can effect hybridization in a manner mimicking an 'A' base such as 2,6-diaminopurine might be selected should other consideration, e.g., stronger hybridization (relative to hybridization achieved with adenine), be desired.

Sugar Modifications: For each nucleoside of an oligonucleotide, the sugar portion of the nucleoside may be selected from a large palette of different sugar or sugar surrogate units available. These may be modified sugar groups, for instance sugars containing one or more substituent groups. Preferred substituent groups comprise the following at the 2' position: OH; F; O-, S-, or N-alkyl, O-, S-, or N-alkenyl, or O, S- or N-alkynyl, wherein the alkyl, alkenyl and alkynyl may be substituted or unsubstituted C$_1$ to C$_{10}$ alkyl or C$_2$ to C$_{10}$ alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. Other preferred substituent groups comprise one of the following at the 2' position: C$_1$ to C$_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., *Helv. Chim. Acta*, 1995, 78, 486) i.e., an alkoxyalkoxy group. A further preferred modification includes 2'-dimethylamino oxyethoxy, i.e., a O(CH$_2$)$_2$ON (CH$_3$)$_2$ group, also known as 2'-DMAOE, as described in co-owned U.S. patent application Ser. No. 09/016,520, filed on Jan. 30, 1998, the contents of which are herein incorporated by reference.

Other preferred modifications include 2'-methoxy 2'-aminopropoxy (2'-OCH$_2$CH$_2$CH$_2$NH$_2$) and 2'-fluoro (2'-F). Similar modifications may also be made at other positions on the sugar group, particularly the 3' position of the sugar on the 3' terminal nucleotide or in 2'-5' linked oligonucleotides and the 5' position of 5' terminal nucleotide. The nucleosides of the oligonucleotides may also have sugar mimetics such as cyclobutyl moieties in place of the pentofuranosyl sugar.

Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053 5,639,873; 5,646,265; 5,658,873; 5,670,633; and 5,700,920, certain of which are commonly owned with the present application, each of which is herein incorporated by reference, together with allowed U.S. patent application Ser. No. 08/468,037, filed on Jun. 5, 1995, which is commonly owned with the present application and is herein incorporated by reference.

Modified Linkages (Backbones): In addition to phosphodiester linkages, specific examples of some preferred modified oligonucleotides envisioned for this invention include those containing modified internucleosidic linkages, depicted as moiety "M" in the compounds described herein. These internucleoside linkages are also referred to as linkers, backbones or oligonucleotide backbones. For forming these nucleoside linkages, a palette of different internucleoside linkages or backbones is available. These include modified oligonucleotide backbones, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalklyphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, certain of which are commonly owned with this application, and each of which is herein incorporated by reference.

Preferred internucleoside linkages for oligonucleotides that do not include a phosphorus atom therein, i.e., for oligonucleosides, have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH component parts.

Representative United States Patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application, and each of which is herein incorporated by reference.

In other preferred oligonucleotides, i.e., oligonucleotide mimetics, both the sugar and the intersugar linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-phosphate backbone of an oligonucleotide is replaced with an amide-containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497.

For the internucleoside linkages, the most preferred embodiments of the invention are oligonucleotides with phosphorothioate backbones and oligonucleosides with heteroatom backbones, and in particular —CH$_2$—NH—O—CH$_2$—, —CH$_2$—N(CH$_3$)—O—CH$_2$— [known as a methylene (methylimino) or MMI backbone], —CH$_2$—O$_2$—N(CH$_3$)—CH$_2$—, —CH$_2$—N(CH$_3$)—N(CH$_3$)—CH$_2$— and —O—N(CH$_3$)—CH$_2$—CH$_2$— [wherein the native phosphodiester backbone is represented as —O—P—O—CH$_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Conjugates: In attaching an effector group to one or more nucleosides or internucleoside linkages of an oligonucleotide, various properties of the oligonucleotide are modified. An "effector group" is a chemical moiety that is capable of carrying out a particular chemical or biological function. Examples of such effector groups include, but are not limited to, an RNA cleaving group, a reporter group, an intercalator, a group for improving the pharmacokinetic properties of an oligonucleotide, or a group for improving the pharmacodynamic properties of an oligonucleotide and other substituents having similar properties. A variety of chemical linkers may be used to conjugate an effector group to an oligonucleotide of the invention.

The 5' and 3' termini of an oligonucleotide may be modified to serve as points of chemical conjugation of, e.g., lipophilic moieties (see immediately subsequent paragraph), intercalating agents (Kuyavin et al., WO 96/32496, published Oct. 17, 1996; Nguyen et al., U.S. Pat. No. 4,835,263, issued May 30, 1989) or hydroxyalkyl groups (Helene et al., WO 96/34008, published Oct. 31, 1996).

Other positions within an oligonucleotide of the invention can be used to chemically link thereto one or more effector groups to form an oligonucleotide conjugate. As an example, U.S. Pat. No. 5,578,718 to Cook et al. discloses methods of attaching an alkylthio linker, which may be further derivatized to include additional groups, to ribofuranosyl positions, nucleosidic base positions, or on internucleoside linkages. Additional methods of conjugating oligonucleotides to various effector groups are known in the art; see, e.g., *Protocols for Oligonucleotide Conjugates* (*Methods in Molecular Biology*, Volume 26) Agrawal, S., ed., Humana Press, Totowa, N.J., 1994.

Another preferred additional or alternative modification of the oligonucleotides of the invention involves chemically linking to the oligonucleotide one or more lipophilic moieties which enhance the cellular uptake of the oligonucleotide. Such lipophilic moieties may be linked to an oligonucleotide at several different positions on the oligonucleotide. Some preferred positions include the 3' position of the sugar of the 3' terminal nucleotide, the 5' position of the sugar of the 5' terminal nucleotide, and the 2' position of the sugar of any nucleotide. The N position of a purine nucleobase may also be utilized to link a lipophilic moiety to an oligonucleotide of the invention (Gebeyehu, G., et al., *Nucleic Acids Res.*, 1987, 15:4513). Such lipophilic moieties include but are not limited to a cholesteryl moiety (Letsinger et al., *Proc. Natl. Acad. Sci. U.S.A.*, 1989, 86:6553), cholic acid (Manoharan et al., *Bioorg. Med. Chem. Let.*, 1994, 4:1053), a thioether, e.g., hexyl-S-tritylthiol (Manoharan et al., *Ann. N.Y. Acad. Sci.*, 1992, 660:306; Manoharan et al., *Bioorg. Med. Chem. Let.*, 1993, 3:2765), a thiocholesterol (Oberhauser et al., *Nucl. Acids Res.*, 1992, 20:533), an aliphatic chain, e.g., dodecandiol or undecyl residues (Saison-Behmoaras et al., *EMBO J.*, 1991, 10:111; Kabanov et al., *FEES Lett.*, 1990, 259:327; Svinarchuk et al., *Biochimie*, 1993, 75:49), a phospholipid, e.g., dihexadecyl-rac-glycerol or triethylammonium 1,2-di-O-hexadecyl-rac-glycero-3-H-phosphonate (Manoharan et al., *Tetrahedron Lett.*, 1995, 36:3651; Shea et al., *Nucl. Acids Res.*, 1990, 18:3777), a polyamine or a polyethylene glycol chain (Manoharan et al., *Nucleosides & Nucleotides*, 1995, 14:969), or adamantane acetic acid (Manoharan et al., *Tetrahedron Lett.*, 1995, 36:3651), a palmityl moiety (Mishra et al., *Biochim. Biophys. Acta*, 1995, 1264:229), or an octadecylamine or hexylamino-carbonyl-oxycholesterol moiety (Crooke et al., *J. Pharmacol. Exp. Ther.*, 1996, 277:923). Oligonucleotides comprising lipophilic moieties, and methods for preparing such oligonucleotides, are disclosed in U.S. Pat. Nos. 5,138,045, 5,218,105 and 5,459,255, the contents of which are hereby incorporated by reference.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the present application, and each of which is herein incorporated by reference.

Oligonucleotide Synthesis: The oligonucleotides used in accordance with this invention may be conveniently and routinely made through the well-known technique of solid phase synthesis. Unsubstituted and substituted phosphodiester oligonucleotides are synthesized on an automated DNA synthesizer (Applied Biosystems model 380B) using standard phosphoramidite chemistry with oxidation by iodine.

Phosphorothioates are synthesized as per the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55 C (18 hr), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or U.S. Pat. No. 5,366,878, hereby incorporated by reference.

Alkylphosphonothioate oligonucleotides are prepared as described in published PCT applications PCT/US94/00902 and PCT/US93/06976 (published as WO 94/17093 and WO 94/02499, respectively).

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Boranophosphate oligonucleotides are prepared as described in U.S. Pat. Nos. 5,130,302 and 5,177,198, both herein incorporated by reference.

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and PO or PS linkages are prepared as described in U.S. Pat. Nos. 5,378,825; 5,386,023; 5,489,677; 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5. They may also be prepared in accordance with U.S. Pat. Nos. 5,539,082; 5,700,922, and 5,719,262, herein incorporated by reference.

Chimeric Oligonucleotides: It is not necessary for all positions in a given compound to be uniformly modified. In fact, more than one of the aforementioned modifications may be incorporated in a single compound or even at a single nucleoside within an oligonucleotide. The present invention also includes compounds which are chimeric compounds. 'Chimeric' compounds or 'chimeras,' in the context of this invention, are compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids.

By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures representing the union of two or more oligonucleotides, modified oligonucleotides, oligonucleosides and/or oligonucleotide mimetics as described above. Such compounds have also been referred to in the art as "hybrids" or "gapmers". Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the present application and each of which is herein incorporated by reference, together with commonly owned and allowed U.S. patent application Ser. No. 08/465,880, filed on Jun. 6, 1995, also herein incorporated by reference.

Chimeric oligonucleotides, oligonucleosides or mixed oligonucleotides/oligonucleosides of the invention can be of several different types. These include a first type wherein the 'gap' segment of linked nucleosides is positioned between 5' and 3' 'wing' segments of linked nucleosides and a second 'open end' type wherein the 'gap' segment is located at either the 3' or the 5' terminus of the oligomeric compound. Oligonucleotides of the first type are also known in the art as 'gapmers' or gapped oligonucleotides. Oligonucleotides of the second type are also known in the art as 'hemimers' or 'winymers.'

[2'-O-Me]-[2'-deoxy]-[2'-O-Me] Chimeric Phosphorothioate Oligonucleotides Chimeric oligonucleotides having 2'-O-alkyl phosphorothioate and 2'-deoxy phosphorothioate oligonucleotide segments are synthesized using 2'-deoxy-5'-dimethoxytrityl-3'-O-phosphoramidites for the DNA portion and 5'-dimethoxytrityl-2'-O-methyl-3'-O-phosphoramidites for 5' and 3' wings. The standard synthesis cycle is modified by increasing the wait step after the delivery of tetrazole and base to 600 s repeated four times for DNA and twice for 2'-O-methyl. The fully protected oligonucleotide was cleaved from the support and the phosphate group is deprotected in 3:1 Ammonia/Ethanol at room temperature overnight then lyophilized to dryness. Treatment in methanolic ammonia for 24 hrs at room temperature is done to deprotect all bases and the samples are again lyophilized to dryness.

[2'-O-(2-Methoxyethyl)]-[2'-deoxy]-[2'-O-(Methoxyethyl)] Chimeric Phosphorothioate Oligonucleotides: [2'-O-(2-methoxyethyl)]-[2'-deoxy]-[-2'-O-(methoxyethyl)] chimeric phosphorothioate oligonucleotides are prepared as per the procedure above for the 2'-O-methyl chimeric oligonucleotide, with the substitution of 2'-O-(methoxy-ethyl)amidites for the 2'-O-methyl amidites.

[2'-O-(2-methoxyethyl) phosphodiester]-[2'-deoxy phosphorothioate]-[2'-O-(2-Methoxyethyl) Phosphodiester] Chimeric Oligonucleotide: [2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites in the wing portions. Sulfurization utilizing 3,H-1,2 benzodithiole-3-one 1,1 dioxide (Beaucage Reagent) is used to generate the phosphorothioate internucleotide linkages within the wing portions of the chimeric structures. Oxidization with iodine is used to generate the phosphodiester internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

The present invention also includes oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (Cook et al., U.S. Pat. No. 5,587,361) and those having substantially chirally pure (Sp or Rp) alkylphosphonate, phosphoamidate or phosphotriester linkages (Cook, U.S. Pat. Nos. 5,212,295 and 5,521,302).

Examples of specific oligonucleotides and the target genes to which they inhibit which may be employed in formulations of the present invention include:

```
                                          (SEQ ID NO: 1)
ISIS-15839    GCCCA AGCTG GCATC CGTCA    ICAM-1

(SEQ ID NO: 2)
ISIS-13312    GCGTT TGCTC TTCTT CTTGC G  HCMV (SEQ ID NO: 3)
ISIS-9605     GTTCT CGCTG GTGAG TTTCA    PKCα

(SEQ ID NO: 3)
ISIS-9606     GTTCT CGCTG GTGAG TTTCA    PKCα

(SEQ ID NO: 4)
ISIS-14859    AACTT GTGCT TGCTC          PKCα

(SEQ ID NO: 5)
ISIS-17709    GCCAA GGAGT TTGAG ATAGT    akt-2

(SEQ ID NO: 6)
ISIS-17044    CCGCA GCCAT GCGCT CTTGG    VLA-4

(SEQ ID NO: 7)
ISIS-28089    GTGTG CCAGA CACCC TATCT    TNFα

(SEQ ID NO: 8)
ISIS-104838   GCTGA TTAGA GAGAG GTCCC    TNFα
``` wherein (i) each oligo backbone linkage is a phosphorothioate linkage (except ISIS-9605 and ISIS-17709) and (ii) each sugar is 2'-deoxy unless represented in bold font in which case it incorporates a 2'-O-methoxyethyl group and (iii) underlined cytosine nucleosides incorporate a 5-methyl substituent on their nucleobase. ISIS-9605 incorporates natural phosphodiester bonds at the first five and last five linkages with the remainder being phosphorothioate linkages. ISIS-17709 incorporates natural phosphodiester bonds at the first four and last four linkages with the remainder being phosphorothiate linkages.

The formulation of pharmaceutical compositions and their subsequent administration is believed to be within the skill of those in the art. Specific comments regarding the present invention are presented below.

Therapeutic Considerations: In general, for therapeutic applications, a patient (i.e., an animal, including a human, having, suspected of having, or predisposed to a disease or disorder) is administered one or more nucleic acids, including oligonucleotides, in accordance with the invention in doses ranging from 0.01 ug to 100 g per kg of body weight depending on the age of the patient and the severity of the disorder or disease state being treated. Further, the treatment regimen may last for a period of time which will vary depending upon the nature of the particular disease or disorder, its severity and the overall condition of the patient, and may extend from once daily to once every 20 years. In the context of the invention, the term "treatment" or "treatment regimen" is meant to encompass therapeutic, palliative and prophylactic modalities. Following treatment, the patient is monitored for changes in his/her condition and for alleviation of the symptoms of the disorder or disease state. The dosage of the nucleic acid may either be increased in the event the patient does not respond significantly to current dosage levels, or the dose may be decreased if an alleviation of the symptoms of the disorder or disease state is observed, or if the disorder or disease state has been ablated.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to 20 years. An optimal dosing schedule is used to deliver a therapeutically effective amount of the nucleic acid being administered via a particular mode of administration.

The term "therapeutically effective amount," for the purposes of the invention, refers to the amount of nucleic acid-containing formulation which is effective to achieve an intended purpose without undesirable side effects (such as toxicity, irritation or allergic response). Although individual needs may vary, determination of optimal ranges for effective amounts of formulations is within the skill of the art. Human doses can be extrapolated from animal studies (Katocs et al., Chapter 27 In: Remington's Pharmaceutical Sciences, 18th Ed., Gennaro, ed., Mack Publishing Co., Easton, Pa., 1990). Generally, the dosage required to provide an effective amount of a formulation, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s) (Nies et al., Chapter 3 In: Goodman & Gilman's The Pharmacological Basis of Therapeutics, 9th Ed., Hardman et al., eds., McGraw-Hill, New York, N.Y., 1996).

As used herein, the term "high risk individual" is meant to refer to an individual for whom it has been determined, via, e.g., individual or family history or genetic testing, has a significantly higher than normal probability of being susceptible to the onset or recurrence of a disease or disorder. As art of treatment regimen for a high risk individual, the individual can be prophylactically treated to prevent the onset or recurrence of the disease or disorder. The term "prophylactically effective amount" is meant to refer to an amount of a formulation which produces an effect observed as the prevention of the onset or recurrence of a disease or disorder. Prophylactically effective amounts of a formulation are typically determined by the effect they have compared to the effect observed when a second formulation lacking the active agent is administered to a similarly situated individual.

Following successful treatment, it may be desirable to have the patient undergo maintenance therapy to prevent the recurrence of the disease state, wherein the nucleic acid is administered in maintenance doses, ranging from 0.01 ug to 100 g per kg of body weight, once or more daily, to once every 20 years. For example, in the case of in individual known or suspected of being prone to an autoimmune or inflammatory condition, prophylactic effects may be achieved by administration of preventative doses, ranging from 0.01 ug to 100 g per kg of body weight, once or more daily, to once every 20 years. In like fashion, an individual may be made less susceptible to an inflammatory condition that is expected to occur as a result of some medical treatment, e.g., graft versus host disease resulting from the transplantation of cells, tissue or an organ into the individual.

The compositions of the present invention can include sterile aqueous solutions which may also contain buffers, diluents and other suitable additives.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both.

5. Bioequivalents

A. Pharmaceutically Acceptable Salts: The compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to "pharmaceutically acceptable salts" of the penetration enhancers and nucleic acids of the invention and prodrugs of such nucleic acids. "Pharmaceutically acceptable salts" are physiologically and pharmaceutically acceptable salts of the penetration enhancers and nucleic acids of the invention: i.e., salts that retain the desired biological activity of the parent compound and do not impart undesired toxicological effects thereto.

The term "pharmaceutically acceptable salts" refers to physiologically and pharmaceutically acceptable salts of the oligonucleotide and nucleic acid compounds employed in the compositions of the present invention (i.e., salts that retain the desired biological activity of the parent compound and do not impart undesired toxicological effects thereto).

Pharmaceutically acceptable base addition salts are formed with metals or amines, such as alkali and alkaline earth metals or organic amines. Examples of metals used as cations are sodium, potassium, magnesium, calcium, ammonium, polyamines such as spermine and spermidine, and the like. Examples of suitable amines are chloroprocaine, choline, N,N'-dibenzylethylenediamine, diethanolamine, dicyclohexylamine, ethylenediamine, N-methylglucamine, and procaine (see, for example, Berge et al., "Pharmaceutical Salts," *J. of Pharma Sci.*, 1977, 66:1). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

B. Oligonucleotide Prodrugs:

The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993.

C. Oligonucleotide Deletion Derivatives:

During the process of oligonucleotide synthesis, nucleoside monomers are attached to the chain one at a time in a repeated series of chemical reactions such as nucleoside monomer coupling, oxidation, capping and detritylation. The stepwise yield for each nucleoside addition is above 99%. That means that less than 1% of the sequence chain failed to the nucleoside monomer addition in each step as the total results of the incomplete coupling followed by the incomplete capping, detritylation and oxidation (Smith, Anal. Chem., 1988, 60, 381A). All the shorter oligonucleotides, ranging from (n-1), (n-2), etc., to 1-mers (nucleotides), are present as impurities in the n-mer olignucleotide product. Among the impurities, (n-2)-mer and shorter oligonucleotide impurities are present in very small amounts and can be easily removed by chromatographic purification (Warren et al., Chapter 9 *In: Methods in Molecular Biology*, Vol. 26: *Protocols for Oligonucleotide Conjugates*, Agrawal, S., Ed., 1994, Humana Press Inc., Totowa, N.J., pages 233-264). However, due to the lack of chromatographic selectivity and product yield, some (n−1)-mer impurities are still present in the full-length (i.e., n-mer) oligonucleotide product after the purification process. The (n−1) portion consists of the mixture of all possible single base deletion sequences relative to the n-mer parent oligonucleotide. Such (n−1) impurities can be classified as terminal deletion or internal deletion sequences, depending upon the position of the missing base (i.e., either at the 5' or 3' terminus or internally). When an oligonucleotide containing single base deletion sequence impurities is used as a drug (Crooke, *Hematologic Pathology*, 1995, 9, 59), the terminal deletion sequence impurities will bind to the same target mRNA as the full length sequence but with a slightly lower affinity. Thus, to some extent, such impurities can be considered as part of the active drug component, and are thus considered to be bioequivalents for purposes of the present invention.

6. Exemplary Utilities of the Invention:

The compositions and methods of the present invention are useful for the treatment of a wide variety of disorders including asthma, cancers of the lung, pulmonary fibrosis, and various infectious diseases of the lung, including rhinovirus, tuberculosis, bronchitis, and pneumonia.

Two important events that occur at the cellular level and which contribute to asthmatic responses are (1) the infiltration of the airway lumen by leukocytes and (2) the activation of T lymphocytes (T cells) from the $T_H0$ to the $T_H2$ state and the subsequent production and release of pro-inflammatory cytokines by activated T cells. Molecules that mediate either or both of these processes are potential targets for asthma therapy.

ICAM-1 has been implicated in the pathogenesis of asthma, and a monoclonal antibody to ICAM-1 attenuates eosinophilia and hyperresponsiveness (Wegner et al., *Science*, 1990, 247, 456). Antisense compounds targeted to ICAM-1 are described in U.S. Pat. Nos. 5,514,788 and 5,591,623, and copending U.S. patent application Ser. Nos. 09/009,490 and 09/062,416, Jan. 20, 1998 and Apr. 17, 1998, respectively, all to Bennett et al., each of which are incorporated herein their entirety.

Adhesion molecule-mediated recruitment of eosinophils and other leukocytes has been implicated in mechanisms of asthmatic inflammation (Bochner et al., *Annu. Rev. Immunol.*, 1994, 12, 295). In addition to ICAM-1, adhesion molecules of particular interest include ELAM-1 (a.k.a. E-selectin) and VCAM-1. Antibody to ELAM-1 prevents neutrophil accumulation in monkey lungs (Gundel et al., *J. Clin. Invest.*, 1991, 88, 1407). Antisense compounds targeted to the adhesions molecules ELAM-1 and VCAM-1 are described in U.S. Pat. Nos. 5,514,788 and 5,591,623.

It has been hoped that inhibitors of ICAM-1, VCAM-1, and ELAM-1 expression would provide a novel therapeutic class of anti-inflammatory agents with activity towards a wide variety of inflammaotry diseases, or diseases within inflammatory component such as asthma. The use of neutralizing monoclonal antibodies against ICAM-1 in animal models provide ample evidence that such inhibitors if identified would have therapeutic benefit for asthma. See Wegner et al., *Science* 1990, 247, 456-459.

B7-1 and B7-2 are thought to be the primary molecules expressed on professional antigen presenting cells, (APCs) (see Liu and Linsley, *Curr. Opin. Immunol.*, 1992, 4, 265). The B7 proteins are thought to provide an essential signal for differentiation of T cells ($T_H0$ lymphocytes) and to contribute to the activation of memory cells. Antisense compounds targeted to B7 proteins are described in copending U.S. patent application Ser. No. 08/777,266, filed Dec. 31, 1996, to Bennett et al.

Another molecule expressed on APCs and which stimulates T cell activation is CD40 (for a review, see Banchereau et al., *Annu. Rev. Immunol.*, 1994, 12, 881). Antisense compounds targeted to CD40 are described in copending U.S. patent application Ser. No. 09/071,433, filed May 1, 1998, to Bennett et al.

Yet another molecule expressed on APCs and which stimulates T cell activation is LFA-3 (see Liu and Linsley, *Curr. Opin. Immunol.*, 1992, 4, 265). Antisense compounds targeted to LFA-3 are described in copending U.S. patent application Ser. No. 09/045,106, filed Mar. 20, 1998, to Bennett et al.

PECAM-1 proteins are glycoproteins which are expressed on the surfaces of a variety of cell types (for reviews, see Newman, J. Clin. Invest., 1997, 99, 3 and DeLisser et al., *Immunol. Today*, 1994, 15, 490). In addition to directly participating in cell-cell interactions, PECAM-1 apparently also regulates the activity and/or expression of other molecules involved in cellular interactions (Litwin et al., *J. Cell Biol.*, 1997, 139, 219) and is thus a key mediator of several cell:cell interactions. Antisense compounds targeted to PECAM-1 are described in copending U.S. patent application Ser. No. 09/044,506, filed Mar. 19, 1998, to Bennett et al.

The compositions and methods of the present invention are useful for the treatment of cancers of the lung. For example, antisense oligonucleotides directed to any of a number of molecular targets involved in tumorigenesis, maintenance of the hyperproliferative state and metastasis can targeted to prevent or inhibit lung cancers, or to prevent their spread to other tissues.

The ras oncogenes are guanine-binding proteins that have been implicated in cancer by, e.g., the fact that activated ras oncogenes have been found in about 30% of human tumors generally; this figure approached 100% in carcinomas of the exocrine pancreas (for a review, see Downward, *Trends in Biol. Sci.*, 1990, 15, 469). Further, intratracheal installation of a retroviral antisense K-ras construct prevents orthotopic human lung cancer growth in an animal model, demonstrating the potential of antisense approaches to lung cancer (Georges, R. N., et al., *Cancer Research*, 1993, 53, 1743). Antisense compounds targeted to H-ras and K-ras are described in U.S. Pat. Nos. 5,582,972 to Lima et al., 5,582,986 to Monia et al. and 5,661,134 to Cook et al., and in published PCT application WO 94/08003, the disclosures of which are incorporated by reference herein in their entirety.

Protein Kinase C (PKC) proteins have also been implicated in tumorigenesis. Antisense compounds targeted to Protein Kinase C (PKC) proteins are described in U.S. Pat. Nos. 5,620,963 to Cook et al. and 5,681,747 to Boggs et al.

The compositions and methods of the present invention are useful for the treatment of Pulmonary Fibrosis. Phan (*Thorax*, 1995, 50, 415) reviews current beliefs regarding pulmonary fibrosis, and notes that potential targets for therapy include cell adhesion and/or T cell stimulatory molecules (e.g., ICAM-1, ELAM-1, VCAM-1, B7 proteins, CD40, LFA-3, PECAM-1, supra). Antisense oligonucleotides targeted for one or more of these proteins are amenable for use in the compositions and methods of the invention.

The compositions and methods of the present invention also find use in the treatment and/or prevention of rhinovirus. For example, it has been proposed that ICAM-1 is the cellular receptor for the major serotype of rhinovirus, which accounts for greater than 50% of common colds (Staunton et al., *Cell*, 1989, 56, 849; Greve et al., *Cell*, 1989, 56, 839).

The compositions and methods of the present invention also find use in the treatment of tuberculosis. For example, antisense compounds targeted to the pathogens *Mycobacterium tuberculosis* or *M. bovis* can be administered to a patient in accordance with the methods of the invention.

In instances where acute bronchitis is a result of infection, bronchitis can be treated by administration in accordance with the methods of the invention of compositions of the invention containing one or more antisense compounds targeted to the appropriate pathogen(s).

The compositions and methods of the present invention also find use in the treatment of pneumonia, for example by administration of antisense compounds targeted to the pathogen *Streptococcus pneumoniae*.

In addition to the foregoing, the methods and compositions of the invention are also directed to antisense oligonucleotides targeted to genes that are implicated in other lung disorders. These include, for example, viruses which infect the lung (e.g. respiratory syncytial virus, H. Influenzae, parainfluenza), obstructive lung disorders such as pulmonary embolism or anaphylaxis, chronic obstructive pulmonary disease (COPD), emphysema, chronic bronchitis, bronchiectasis and cystic fibrosis.

The invention is drawn to the pulmonary administration of a nucleic acid, such as an oligonucleotide, having biological activity to an animal. By "having biological activity," it is meant that the nucleic acid functions to modulate the expression of one or more genes in an animal as reflected in either absolute function of the gene (such as ribozyme activity) or by production of proteins coded by such genes. In the context of this invention, "to modulate" means to either effect an increase (stimulate) or a decrease (inhibit) in the expression of a gene. Such modulation can be achieved by, for example, an antisense oligonucleotide by a variety of mechanisms known in the art, including but not limited to transcriptional arrest; effects on RNA processing (capping, polyadenylation and splicing) and transportation; enhancement or reduction of cellular degradation of the target nucleic acid; and translational arrest (Crooke et al., *Exp. Opin. Ther. Patents*, 1996, 6:1).

In an animal other than a human, the compositions and methods of the invention can be used to study the function of one or more genes in the animal. For example, antisense oligonucleotides have been systemically administered to rats in order to study the role of the N-methyl-D-aspartate receptor in neuronal death, to mice in order to investigate the biological role of protein kinase C-a, and to rats in order to examine the role of the neuropeptide Y1 receptor in anxiety (Wahlestedt et al., *Nature*, 1993, 363:260; Dean et al., *Proc. Natl. Acad. Sci. U.S.A.*, 1994, 91:11762; and Wahlestedt et al., *Science*, 1993, 259:528, respectively). In instances where complex families of related proteins are being investigated, "antisense knockouts" (i.e., inhibition of a gene by systemic administration of antisense oligonucleotides) may represent the most accurate means for examining a specific member of the family (see, generally, Albert et al., *Trends Pharmacol. Sci.*, 1994, 15:250).

The compositions and methods of the invention are also useful therapeutically, i.e., to provide therapeutic, palliative or prophylactic relief to an animal, including a human, having or suspected of having or of being susceptible to, a disease or disorder that is treatable in whole or in part with one or more nucleic acids. The term "disease or disorder" (1) includes any abnormal condition of an organism or part, especially as a consequence of infection, inherent weakness, environmental stress, that impairs normal physiological functioning; (2) excludes pregnancy per se but not autoimmune and other diseases associated with pregnancy; and (3) includes cancers and tumors. The term "having or suspected of having or of being susceptible to" indicates that the subject animal has been determined to be, or is suspected of being, at increased risk, relative to the general population of such animals, of developing a particular disease or disorder as herein defined. For example, a subject animal could have a personal and/or family medical history that includes frequent occurrences of a particular disease or disorder. As another example, a subject animal could have had such a susceptibility determined by genetic screening according to techniques known in the art (see, e.g., U.S. Congress, Office of Technology Assessment, Chapter 5 *In: Genetic Monitoring and Screening in the Workplace*, OTA-BA-455, U.S. Government Printing Office, Washington, D.C., 1990, pages 75-99). The term "a disease or disorder that is treatable in whole or in part with one or more nucleic acids" refers to a disease or disorder, as herein defined, (1) the management, modulation or treatment thereof, and/or (2) therapeutic, palliative and/or prophylactic relief therefrom, can be provided via the administration of more nucleic acids. In a preferred embodiment, such a disease or disorder is treatable in whole or in part with an antisense oligonucleotide.

Preferably, the compounds and method of the invention employ particles containing oligonucleotide therapeutics or diagnostics. The particles can be solid or liquid, and are preferably of respirable size: that is, particles of a size sufficiently small to pass through the mouth and larynx upon inhalation and into the bronchi and alveoli of the lungs. In general, particles ranging from about 5 to 20 microns in size are respirable and are expected to reach the bronchioles (Allen, *Secundum Artem*, Vol. 6, No. 3, May 8, 1998. Retrieved from the Internet: <URL: www.paddocklabs.com/secundum/secaindx.html. It is greatly desirable to avoid particles of non-respirable size, as these tend to deposit in the throat and be swallowed, thus reducing the quantity of oligonucleotide reaching the lung.

Liquid pharmaceutical compositions of oligonucleotide can be prepared by combining the oligonucleotide with a suitable vehicle, for example sterile pyrogen free water, or saline solution. Other therapeutic compounds may optionally be included.

The present invention also contemplates the use of solid particulate compositions. Such compositions preferably comprise particles of oligonucleotide that are of respirable size. Such particles can be prepared by, for example, grinding dry oligonucleotide by conventional means, fore example with a mortar and pestle, and then passing the resulting powder composition through a 400 mesh screen to segregate large particles and agglomerates. A solid particulate composition comprised of an active oligonucleotide can optionally contain a dispersant which serves to facilitate the formation of an aerosol, for example lactose.

In accordance with the methods of the present invention, oligonucleotide compositions are aerosolized. Aerosolization of liquid particles can be produced by any suitable means, such as with a nebulizer. See, for example, U.S. Pat. No. 4,501,729. Nebulizers are commercially available devices which transform solutions or suspensions into a therapeutic aerosol mist either by means of acceleration of a compressed gas, typically air or oxygen, through a narrow venturi orifice or by means of ultrasonic agitation. Suitable nebulizers include those sold by Blairex under the name PARI LC PLUS, PARI DURA-NEB 2000, PARI-BABY Size, PARI PRONEB Compressor with LC PLUS, PARI WALKHALER Compressor/Nebulizer System, PARI LC PLUS Reusable Nebulizer, and PARI LC Jet+ Nebulizer.

Exemplary formulations for use in nebulizers consist of an oligonucleotide in a liquid, such as sterile, pyragen free water, or saline solution, wherein the oligonucleotide comprises up to about 40% w/w of the formulation. Preferably, the oligonucleotide comprises less than 20% w/w. If desired, further additives such as preservatives (for example, methyl hydroxybenzoate) antioxidants, and flavoring agents can be added to the composition.

Solid particles comprising an oligonucleotide can also be aerosolized using any solid particulate medicament aerosol generator known in the art. Such aerosol generators produce respirable particles, as described above, and further produce reproducible metered dose per unit volume of aerosol. Suitable solid particulate aerosol generators include insufflators and metered dose inhalers. Metered dose inhalers suitable fore used in the art (along with the trade name, manufacturer and indication they are used for) and useful in the present invention include:

Delivery Device Trade Name Manufacturer Indication
Metered Dose Inhaler (MDI)

Alupent—Boehringer Ingelheim Beta-adrenergic bronchodilator

Atrovent—Boehringer Ingelheim Anticholinergic bronchodilator

Aerobid, Aerobid-M—Forest Steriodal Anti-inflammatory

Beclovent, Beconase—Glaxo Wellcome Steriodal Anti-inflammatory

Flovent—Glaxo Wellcome Steriodal Anti-inflammatory

Ventolin—Glaxo Wellcome Beta-adrenergic bronchodilator

Proventil—Key Pharm. Beta-adrenergic bronchodilator

Maxair—3M Pharm. Beta-adrenergic bronchodilator

Azmacort—Rhone-Poulenc Rorer Steriodal Anti-inflammatory

Tilade—Rhone-Poulenc Rorer Anti-inflammatory (inhibits release of inflammatory mediators)

Intal—Rhone-Poulenc Rorer Inhibits mast cell degranulation (Asthma)

Vanceril—Schering Steriodal Anti-inflammatory

Tornalate—Dura Pharm. Beta-adrenergic bronchodilator

Solutions for Nebulization

Alupent—Boehringer Ingelheim Beta-adrenergic bronchodilator

Pulmozyme—Genetech Recombinant human deoxyribonuclease I

Ventolin—Glaxo Wellcome Beta-adrenergic bronchodilator

Tornalate—Dura Pharm. Beta-adrenergic bronchodilator

Intal—Rhone-Poulenc Rorer Inhibits mast cell degranulation (Asthma)

Capsules (powder) for Inhalation Ventolin—Glaxo Wellcome (Rotocaps for use in Rotohaler device) Beta-adrenergic bronchodilator Powder for Inhalation Pulmicort—Astra USA (Turbuhaler device) Steriodal Anti-inflammatory Preferably, liquid or solid aerosols are produced at a rate of from about 10 to 150 liters per minute, more preferably from about 30 to 150 liters per minute, and most preferably about 60 liters per minute.

As used herein, the term "alkyl" includes but is not limited to straight chain, branch chain, and alicyclic hydrocarbon groups. Alkyl groups of the present invention may be substituted. Representative alkyl substituents are disclosed in U.S. Pat. No. 5,212,295, at column 12, lines 41-50.

Further representative 2' sugar modifications amenable to the present invention include fluoro, O-alkyl, O-alkylamino, O-alkylalkoxy, protected O-alkylamino, O-alkylaminoalkyl, O-alkyl imidazole, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi, et al., *Drug Design and Discovery* 1992, 9, 93, Ravasio, et al., *J. Org. Chem.* 1991, 56, 4329, and Delgardo et. al., *Critical Reviews in Therapeutic Drug Carrier Systems* 1992, 9, 249, each of which are hereby incorporated by reference in their entirety. Further sugar modifications are disclosed in Cook, P. D., supra. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions, hereby incorporated by reference in its entirety.

Sugars having O-substitutions on the ribosyl ring are also amenable to the present invention. Representative substitutions for ring 0 include S, $CH_2$, CHF, and $CF_2$, see, e.g., Secrist, et al., *Abstract 21, Program & Abstracts, Tenth International Roundtable, Nucleosides, Nucleotides and their Bio-* logical Applications, Park City, Utah, Sep. 16-20, 1992, hereby incorporated by reference in its entirety.

As used herein, the term "aralkyl" denotes alkyl groups which bear aryl groups, for example, benzyl groups. The term "alkaryl" denotes aryl groups which bear alkyl groups, for example, methylphenyl groups. "Aryl" groups are aromatic cyclic compounds including but not limited to phenyl, naphthyl, anthracyl, phenanthryl, pyrenyl, and xylyl.

In general, the term "hetero" denotes an atom other than carbon, preferably but not exclusively N, O, or S. Accordingly, the term "heterocycloalkyl" denotes an alkyl ring system having one or more heteroatoms (i.e., non-carbon atoms). Preferred heterocycloalkyl groups include, for example, morpholino groups. As used herein, the term "heterocycloalkenyl" denotes a ring system having one or more double bonds, and one or more heteroatoms. Preferred heterocycloalkenyl groups include, for example, pyrrolidino groups.

In some preferred embodiments, the compounds of the invention can comprise a linker connected to a solid support. Solid supports are substrates which are capable of serving as the solid phase in solid phase synthetic methodologies, such as those described in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069. Linkers are known in the art as short molecules which serve to connect a solid support to functional groups (e.g., hydroxyl groups) of initial synthon molecules in solid phase synthetic techniques. Suitable linkers are disclosed in, for example, *Oligonucleotides And Analogues A Practical Approach*, Ekstein, F. Ed., IRL Press, N.Y, 1991, Chapter 1, pages 1-23, hereby incorporated by reference in its entirety.

Solid supports according to the invention include those generally known in the art to be suitable for use in solid phase methodologies, including, for example, controlled pore glass (CPG), oxalyl-controlled pore glass (see, e.g., Alul, et al., *Nucleic Acids Research* 1991, 19, 1527, hereby incorporated by reference in its entirety), TentaGel Support—an aminopolyethyleneglycol derivatized support (see, e.g., Wright, et al., *Tetrahedron Letters* 1993, 34, 3373, hereby incorporated by reference in its entirety) and Poros—a copolymer of polystyrene/divinylbenzene.

Some preferred embodiments of the invention comprise one or more hydroxyl protecting groups. A wide variety of hydroxyl protecting groups can be employed in the methods of the invention. Preferably, the protecting group is stable under basic conditions but can be removed under acidic conditions. In general, protecting groups render chemical functionalities inert to specific reaction conditions, and can be appended to and removed from such functionalities in a molecule without substantially damaging the remainder of the molecule. Representative hydroxyl protecting groups are disclosed by Beaucage, et al., *Tetrahedron* 1992, 48, 2223-2311, and also in Greene and Wuts, *Protective Groups in Organic Synthesis*, Chapter 2, 2d ed, John Wiley & Sons, New York, 1991, each of which are hereby incorporated by reference in their entirety. Preferred protecting groups used for $R_2$, $R_3$ and $R_{3a}$, include dimethoxytrityl (DMT), monomethoxytrityl, 9-phenylxanthen-9-yl (Pixyl) and 9-(p-methoxyphenyl)xanthen-9-yl (Mox). The $R_2$ or $R_3$ group can be removed from oligomeric compounds of the invention by techniques well known in the art to form the free hydroxyl. For example, dimethoxytrityl protecting groups can be removed by protic acids such as formic acid, dichloroacetic acid, trichloroacetic acid, p-toluene sulphonic acid or with Lewis acids such as for example zinc bromide. See for example, Greene and Wuts, supra.

In some preferred embodiments of the invention amino groups are appended to alkyl or other groups, such as, for example, 2'-alkoxy groups (e.g., where $R_1$ is alkoxy). Such amino groups are also commonly present in naturally occurring and non-naturally occurring nucleobases. It is generally preferred that these amino groups be in protected form during the synthesis of oligomeric compounds of the invention. Representative amino protecting groups suitable for these purposes are discussed in Greene and Wuts, *Protective Groups in Organic Synthesis*, Chapter 7, 2d ed, John Wiley & Sons, New York, 1991. Generally, as used herein, the term "protected" when used in connection with a molecular moiety such as "nucleobase" indicates that the molecular moiety contains one or more functionalities protected by protecting groups.

The oligomeric compounds of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

EXAMPLES

The following examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

Example 1

Preparation of Oligonucleotides

A. General Synthetic Techniques:

Oligonucleotides were synthesized on an automated DNA synthesizer using standard phosphoramidite chemistry with oxidation using iodine. Beta-cyanoethyldiisopropyl phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one-1,1-dioxide in acetonitrile for the stepwise thiation of the phosphite linkages.

The synthesis of 2'-O-methyl- (a.k.a. 2'-methoxy-) phosphorothioate oligonucleotides is according to the procedures set forth above substituting 2'-O-methyl b-cyanoethyldiisopropyl phosphoramidites (Chemgenes, Needham, Mass.) for standard phosphoramidites and increasing the wait cycle after the pulse delivery of tetrazole and base to 360 seconds.

Similarly, 2'-O-propyl- (a.k.a 2'-propoxy-) phosphorothioate oligonucleotides are prepared by slight modifications of this procedure and essentially according to procedures disclosed in U.S. patent application Ser. No. 08/383,666, filed Feb. 3, 1995, which is assigned to the same assignee as the instant application and which is incorporated by reference herein.

The 2'-fluoro-phosphorothioate oligonucleotides of the invention are synthesized using 5'-dimethoxytrityl-3'-phosphoramidites and prepared as disclosed in U.S. patent application Ser. No. 08/383,666, filed Feb. 3, 1995, and U.S. Pat. No. 5,459,255, which issued Oct. 8, 1996, both of which are assigned to the same assignee as the instant application and which are incorporated by reference herein. The 2'-fluoro-oligonucleotides are prepared using phosphoramidite chemistry and a slight modification of the standard DNA synthesis protocol (i.e., deprotection was effected using methanolic ammonia at room temperature).

PNA antisense analogs are prepared essentially as described in U.S. Pat. Nos. 5,539,082 and 5,539,083, both of which (1) issued Jul. 23, 1996, (2) are assigned to the same assignee as the instant application and (3) are incorporated by reference herein.

Oligonucleotides comprising 2,6-diaminopurine are prepared using compounds described in U.S. Pat. No. 5,506,351 which issued Apr. 9, 1996, and which is assigned to the same assignee as the instant application and incorporated by reference herein, and materials and methods described by Gaffney et al. (*Tetrahedron*, 1984, 40:3), Chollet et al., (*Nucl. Acids Res.*, 1988, 16:305) and Prosnyak et al. (*Genomics*, 1994, 21:490). Oligonucleotides comprising 2,6-diaminopurine can also be prepared by enzymatic means (Bailly et al., *Proc. Natl. Acad. Sci. U.S.A.*, 1996, 93:13623).

The 2'-methoxyethoxy oligonucleotides of the invention were synthesized essentially according to the methods of Martin et al. (*Helv. Chim. Acta*, 1995, 78, 486). For ease of synthesis, the 3' nucleotide of the 2'-methoxyethoxy oligonucleotides was a deoxynucleotide, and 2'-O—$CH_2CH_2OCH_3$ cytosines were 5-methyl cytosines, which were synthesized according to the procedures described below.

B. Synthesis of 5-Methyl Cytosine Monomers:

1. 2,2'-Anhydro[1-(β-D-arabinofuranosyl)-5-methyluridine]: 5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to N,N-dimethylformamide (DMF, 300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2. 2'-O-Methoxyethyl-5-methyluridine: 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155-160° C., the vessel was opened and the solution evaporated to dryness and triturated with methanol (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/methanol (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

3. 2'-O-Methoxyethyl-5'-O-dimethoxytrityl-5-methyluridine: 2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. High pressure liquid chromatography (HPLC) showed the presence of approximately 70% product. The solvent was evaporated and triturated with $CH_3CN$ (200 mL). The residue was dissolved in $CHCl_3$ (1.5 L) and extracted with ×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

4. 3'-O-Acetyl-2'-O-methoxyethyl-5'-O-dimethoxytrityl-5-methyluridine: 2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by thin layer chromatography (tlc) by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approximately 90% product). The residue was purified on a 3.5 kg silica gel column and eluted using EtOAc/Hexane (4:1). Pure product fractions were evaporated to yield 96 g (84%).

5. 3'-O-Acetyl-2'-O-methoxyethyl-5'-0-dimethoxytrityl-5-methyl-4-triazoleuridine: A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0-10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

6. 2'-O-Methoxyethyl-5'-O-dimethoxytrityl-5-methylcytidine: A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. Methanol (400 mL) saturated with NH, gas was added and the vessel heated to 100° C. for 2 hours (thin layer chromatography, tlc, showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

7. N$^4$-Benzoyl-2'-O-methoxyethyl-5'-O-dimethoxytrityl-5-methylcytidine: 2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$, (700 mL) and extracted with saturated NaHCO$_3$ (×300 mL) and saturated NaCl (×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

8. N$^4$-Benzoyl-2'-O-methoxyethyl-5'-O-dimethoxytrityl-5-methylcytidine-3'-amidite: N$^4$-Benzoyl-2-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc\Hexane (3:1) as the eluting solvent. The pure fractions were combined to give 90.6 g (87%) of the title compound.

C. Oligonucleotide Purification: After cleavage from the controlled pore glass (CPG) column (Applied Biosystems) and deblocking in concentrated ammonium hydroxide, at 55° C. for 18 hours, the oligonucleotides were purified by precipitation x from 0.5 M NaCl with 2.5 volumes of ethanol followed by further purification by reverse phase high liquid pressure chromatography (HPLC). Analytical gel electrophoresis was accomplished in 20% acrylamide, 8 M urea and 45 mM Tris-borate buffer (pH 7).

D. Oligonucleotide Labeling: Antisense oligonucleotides were labeled in order to detect the presence of and/or measure the quantity thereof in samples taken during the course of the in vivo pharmacokinetic studies described herein. Although radiolabeling by tritium exchange is one preferred means of labeling antisense oligonucleotides for such in vivo studies, a variety of other means are available for incorporating a variety of radiological, chemical or enzymatic labels into oligonucleotides and other nucleic acids.

1. Tritium Exchange: Essentially, the procedure of Graham et al. (*Nucleic Acids Research,* 1993, 21:3737) was used to label oligonucleotides by tritium exchange. Specifically, about 24 mg of oligonucleotide was dissolved in a mixture of 200 uL of sodium phosphate buffer (pH 7.8), 400 uL of 0.1 mM EDTA (pH 8.3) and 200 uL of deionized water. The pH of the resulting mixture was measured and adjusted to pH 7.8 using 0.095 N NaOH. The mixture was lyophilized overnight in a 1.25 mL gasketed polypropylene vial. The oligonucleotide was dissolved in 8.25 uL of b-mercaptoethanol, which acts as a free radical scavenger (Graham et al., *Nucleic Acids Research,* 1993, 21:3737), and 400 uL of tritiated H$_2$O (5 Ci/gram). The tube was capped, placed in a 90BC oil bath for 9 hours without stirring, and then briefly centrifuged to remove any condensate from the inside lid of the tube. (As an optional analytical step, two 10 uL aliquots (one for HPLC analysis, one for PAGE analysis) were removed from the reaction tube; each aliquot was added to a separate 1.5 mL standard microfuge tube containing 490 uL of 50 uM sodium phosphate buffer (pH 7.8).) The oligonucleotide mixture is then frozen in liquid nitrogen and transferred to a lyophilization apparatus wherein lyophilization was carried out under high vacuum, typically for 3 hours. The material was then resuspended in mL of double-distilled H$_2$O and allowed to exchange for 1 hour at room temperature. After incubation, the mixture was again quick frozen and lyophilized overnight. (As an optional analytical step, about 1 mg of the oligonucleotide material is removed for HPLC analysis.) Three further lyophilizations were carried out, each with approximately 1 mL of double-distilled H$_2$O, to ensure the removal of any residual, unincorporated tritium. The final resuspended oligonucleotide solution is transferred to a clean polypropylene vial and assayed. The tritium labeled oligonucleotide is stored at about −70BC.

2. Other Means of Labeling Nucleic Acids:

As is well known in the art, a variety of means are available to label oligonucleotides and other nucleic acids and to separate unincorporated label from the labeled nucleic acid. For example, double-stranded nucleic acids can be radiolabeled by nick translation and primer extension, and a variety of nucleic acids, including oligonucleotides, can be terminally radiolabeled by the use of enzymes such as T4 polynucleotide kinase or terminal deoxynucleotidyl transferase (see, generally, Chapter 3 *In: Short Protocols in Molecular Biology,* 2d Ed., Ausubel et al., eds., John Wiley & Sons, New York, N.Y., pages 3-11 to 3-38; and Chapter 10 *In: Molecular Cloning: A Laboratory Manual,* 2d Ed., Sambrook et al., eds., pages 10.1 to 10.70). It is also well known in the art to label oligonucleotides and other nucleic acids with nonradioactive labels such as, for example, enzymes, fluorescent moieties and the like (see, for example, Beck, *Methods in Enzymology,* 1992, 216: 143; and Ruth, Chapter 6 *In: Protocols for Oligonucleotide Conjugates* (*Methods in Molecular Biology,* Volume 26) Agrawal, S., ed., Humana Press, Totowa, N.J., 1994, pages 167-185).

Example 2

Inhalation Exposure of Oligonucleotides in Mice

1. Nebulization of oligonucleotides.

Aqueous solutions of oligonucleotides were nebulized, and the resulting aerosol was delivered to an animal model (male CD-1 mice) via a nose-only inhalation system. In order to reach the bronchiolar and alveolar regions of the lung, the particle size was targeted for 1 to 5 μm. Following single or multiple exposures, mice were evaluated for signs of toxicity and designated tissues were collected for assessment of organ-specific effects and the oligonucleotide concentrations. The male CD-1 mouse was chosen as the animal model for this study since considerable scientific data is available for this species.

2. Oligonucleotides Employed in Animal Studies

The following compounds were tested in this study:

1) ISIS 2105, a phosphorothioate antisense 2'-deoxyribose oligonucleotide targeted to HPV, and having the sequence: 5'-TTG-CTT-CCA-TCT-TCC-TCG-TC-3' (SEQ ID NO: 9)

2) ISIS 17009, a phosphorothioate antisense 2'-deoxyribose oligonucleotide targeted to mouse ICAM-1, having the sequence: 5'-GGA-GTC-CAG-CAC-TAG-CAC-TG-3' (SEQ ID NO: 10)

3) ISIS 15163, a phosphodiester antisense 2'-O-methoxyethyl oligonucleotide targeted to mouse ICAM-1 (isosequence derivative of 17009) having the sequence: 5'-GGA-GTC-CAG-CAC-TAG-CAC-TG-3' (SEQ ID NO: 10), wherein each C is substituted by 5-methylcytosine.

Sterile sodium chloride (saline) for injection was used to formulate solutions of oligonucleotide, and sodium chloride for injection was used as the control article.

3. Single Exposure of Isis 2105 in Mice

Mice were given a 30 minute nose-only exposure of solutions of ISIS-2105 having concentrations of either 10 or 100 mg/ml, with saline controls. Calculated lung doses (see infra) were 1.2 and 12 mg/kg, respectively. Animals were necropsied at 0 minutes (at the end of exposure), 2 hours, 8 hours, and 24 hours. Animals were generally assessed for their health, and more limited assessments were made of lung tolerability. Lung concentrations of oligonucleotide and oligonucleotide metabolites were performed by capillary gel electrophoresis (CGE) and distribution of oligonucleotide within lung tissue was determined immunohistologically.

Results:

1. General Animal Health

The control group and the low dose group each displayed a 7% or 13% decrease, respectively, in breathing rate during exposure. The high dose group displayed a 28 percent decrease in breathing rate during exposure. Exposure had no effect on body weight or organ weight.

2. Histological Assessment of the Lung

Histological results indicated a slight induction of an inflammatory response in the low dose group, possibly attributable to increased macrophages. There was a significant inflammatory response in the high dose group, manifesting an increased number of macrophages, and disruption of alveolar space.

3. Elimination from the Lung (See FIG. 1)

FIG. 1 shows the elimination of oligonucleotide from the lung of mice in this study. It can be seen that elimination appears to be monophasic in the low dose group, and biphasic in the high dose group. However, it may be that integrity was compromised in the high dose group; i.e., the high dose may have overdosed the lung. There was a relatively long half-life for both parent compound and metabolites which, in the case of the full length oligonucleotide, is greater than 20 hours and for the total oligonucleotide is greater than 40 hours. Metabolism of parent oligonucleotide in the lung appears to be faster than clearance rate from the lung, which is consistent with observations made in other organs.

4. Distribution within the Lung

The oligonucleotide was distributed to all cell types in the lung, including bronchiolar and alveolar epithelium, endothelial cells, and alveolar macrophages. In addition, significant concentrations of oligonucleotide and metabolites were found in lung tissue (by CGE analysis): 80 percent of the oligonucleotide was found to be intact at the end of the exposure, with 50 percent remaining intact 8 hours after the exposure, and 20 to 30 percent intact 24 hours after the exposure.

There were significant concentrations of oligonucleotide and metabolites found in BAL (bronchial alveolar lavage). These are shown in Table 1 below:

TABLE 1

| Concentration of ISIS-2105 Found in BAL | | | | |
|---|---|---|---|---|
| 0 hour | 2 hour | 8 hour | 24 hour | |
| 12 mg/kg (76%) | 6.3 µM (49%) | 4.7 µM (31%) | 1.5 µM (>10%) | 1.1 µM | expressed as concentration of total oligonucleotide (% full length)

For the 12 mg/kg group, detectable levels of oligonucleotide and/or metabolite were found in plasma: 0.6 micromolar at 0 hours (52 percent full length), and 0.3 micromolar at 2 hours (38 percent full length). Significant concentrations were found also in the liver; 30 micrograms 24 hours after the exposure; 12-16 percent of intact parent compound. From these data it can be seen that for the high dosage group, that portion of the oligonucleotide that was delivered to plasma, is cleared relatively quickly.

The foregoing data show that high concentrations of oligonucleotide may adversely affect the breathing rate, possibly by airway irritation, or as a result of the relatively high viscosity of the solution. Importantly, pulmonary delivery of oligonucleotide resulted in distribution to all cell types in the lung.

Example 3

Single and Multiple Exposure Study of Oligonucleotides in Mice

1. Exposure System Design and Concepts

The exposure systems used were designed to nebulize the test article solution or saline only. The exposure atmospheres were generated using PARI LC PLUS nebulizers (PARI Respiratory Equipment, Inc, Richmond, Va.). Filtered compressed air was used as the air supply. Airflow rates were set and maintained at levels required to assure a consistent aerosol generation and maintain animal health. Empty ports within the generation chamber provided locations for obtaining samples for gravimetric and particle size determination or analysis.

Atmosphere concentration was determined both gravimetrically (development phase) and by analytical measurements (animal exposure). Glass fiber filters (Gelman #66075, Gelman sciences, Ann Arbor, Mich.) were placed into in-line filter holders. Airflow rates were regulated to sample a known volume of test atmosphere. Immediately after sampling, the filters were collected and the mass concentration calculated. The filter samples were then processed to extract and analyze the test material deposited on the filter. Analytical measurements were used to calculate the inhaled dose. Samples were collected during each exposure in which animals were placed in the chambers.

Particle size was measured with a Mercer style cascade impactor (Chen et al., *Fundam. Appl. Toxicol.*, 1989, 13, 429). The effective cut-off diameters for the impactor ranged from 4.8 microns to 0.30 microns. Particle size was measured for each oligonucleotide tested, following the first and last exposure. The Mass Median Aerodynamic Diameter (MMAD) for the three oligonucleotides ranged from 2.72 to 3.26 and the Geometric Standard Deviation (GSD) ranged from 2.44 to 2.46.

Animals were exposed in nose-only exposure units similar to the design described by Cannon et al (1983), *Amer. Ind. Hyg. Assoc.* 44(12) 923-928. "Open" type restraint tubes were used to aid in the ability of the animals to thermoregulate and elimination of excetia. The pulmonary dose was calculated based on the following equation:

$$\text{Pulmonary Dose} = \frac{RMV \times \text{Concentration} \times \text{Time} \times \text{Deposition Factor}}{\text{Body Weight}}$$

Wherein:

| | |
|---|---|
| RMV = | respiratory minute volume, assumed* to be 0.03 1/min for a 30 gram mouse |
| Concentration = | chamber concentration based on analytical methods |
| Time = | exposure time in minutes |
| Deposition Factor = | fraction that remains in lung, assumed* to be 10% with a particle size of 2 to 3 micrometers. |
| Body Weight = | mean body weight in grams (30 grams was used as the average) |

Based on this equation, and the data obtained following filter analysis, the estimated pulmonary dose for the low, mid, and high dose groups was approximately 0.8, 1.5 and 3.2 mg/kg, respectively.

2. Results:

A. Nebulization of Oligonucleotides

FIG. 1 shows a plot of milligrams oligonucleotide collected in impinger versus time. These data show the successful nebulization of oligonucleotide; i.e., that the oligonucleotide is uniformly nebulized, and that the size of the resultant particles is not altered over time.

B. Toxicity

Data collected for assessment of potential toxicity included clinical observations, body weight, clinical pathology (hematology and serum chemistry), gross necropsy (observations and organ weights) and microscopic examination of selected tissues. There were no clinical observations attributable to oligonucleotide administration. Body weight gain and clinical pathology parameters were all within the normal range for male CD-1 mice. All mice survived to their respective necropsy interval (following either a single or four exposures) and there were no gross observations at necropsy or changes in organ weights.

Microscopic observations were limited to the lungs of 5 of 5 mice in the 4 exposure-high dose ISIS 2105 group, 2 of 5 mice in the 4 exposure-mid dose ISIS 2105 group, and 1 of 4 or 1 of 5 mice in the high dose ISIS 15163 single or multiple exposure groups, respectively. These effects in the lungs were described as a multifocal inflammatory cell infiltrate that was regarded as being minimal in severity. Similar observations have been noted following intravenous administration of oligonucleotides in mice and these effects have been attributed to immune stimulation aspects that occurs in rodents administered this class of compounds.

No other changes were noted in the lungs, and there were no observations of effects noted for the other tissues examined (liver, kidney, spleen, and nasal passages).

C. Organ Distribution

The concentration of each oligonucleotide and its metabolites was determined in tissue samples of lung, liver, kidney and spleen. Table 1 and Table 2 show the concentrations of total oligonucleotide (parent oligonucleotide and oligonucleotide metabolites) in the lung, liver and kidney. Concentrations observed in the lung were dose-dependent and were greater in mice administered four exposures versus a single exposure. Similar concentrations were observed in lungs of mice exposed to the phosphorothioate oligonucleotides, ISIS 2105 and ISIS 17709, while higher concentrations were observed in mice exposed to ISIS 15163, a phosphodiester 2'-methoxyethyl modified oligonucleotide. Minimal concentrations of total oligonucleotide were observed in the liver or kidney of mice exposed to ISIS 2105 or ISIS 17009 and the liver of mice exposed to ISIS 15163. Slightly greater concentrations were observed in the kidney of mice exposed to ISIS 15163, these concentrations were dose- and exposure number-dependent.

TABLE 2

Concentration of Total Oligonucleotide Following A Single Nose-Only Inhalation Exposure in CD-1 Mice

| | | Tissue Type | | |
|---|---|---|---|---|
| Oligonucleotide | | Lung | Liver | Kidney |
| ISIS 2105 | | | | |
| | Low | 27.4 ± 7.5 | NQ | NQ |
| | Middle | 61.7 ± 9.9 | NQ | NQ |
| | High | 62.4 ± 15.3 | NQ | 4.0 ± 3.6 |
| ISIS 17009 | | | | |
| | Low | 22.9 ± 10.8 | 0.4 ± 0.2 | NQ |
| | Middle | 48.6 ± 15.1 | 1.4 ± 2.6 | NQ |
| | High | 71.8 ± 39.2 | 2.5 ± 2.5 | 2.5 ± 2.5 |
| ISIS 15163 | | | | |
| | Low | 26.9 ± 22.2 | NQ | 2.0 ± 1.3 |
| | Middle | 91.1 ± 53.7 | NQ | 10.2 ± 3.5 |
| | High | 255.9 ± 104.3 | NQ | 30.1 ± 13.7 |

TABLE 3

Concentration of Total Oligonucleotide Following Multiple (Four) Nose-Only Inhalation Exposures in CD-1 Mice

| | | Tissue Type | | |
|---|---|---|---|---|
| Oligonucleotide | | Lung | Liver | Kidney |
| ISIS 2105 | | | | |
| | Low | 48.8 ± 20.8 | NQ | NQ |
| | Middle | 105.0 ± 26.3 | 0.2 ± 0.3 | 0.3 ± 0.4 |
| | High | 103.9 ± 31.3 | 1.1 ± 1.6 | NQ |
| ISIS 17009 | | | | |
| | Low | 61.2 ± 16.1 | NQ | NQ |
| | Middle | 75.7 ± 10.8 | 4.7 ± 5.5 | NQ |
| | High | 87.9 ± 33.4 | 0.7 ± 1.4 | NQ |
| ISIS 15163 | | | | |
| | Low | NQ | NQ | 5.3 ± 3.3 |
| | Middle | 110.1 ± 43.7 | NQ | 61.0 ± 64.5 |
| | High | 319.5 ± 84.0 | NQ | 57.2 ± 17.2 |

Note:
NQ = in all animals, or in all animals but one, no oligonucleotide was found at limit of detection.

As can be seen, nose-only inhalation exposure of oligonucleotide was well tolerated in mice. Effects in the lung were limited to a minimal cellular infiltrate that was likely due to the general immune stimulation that occurs in mice administered this class of compounds. Lung was also the tissue with the greatest concentration of oligonucleotide. Minimal oligonucleotide concentrations were observed in the other organs evaluated, and no histologic alterations were observed in these organs. Similar observations were noted for the phosphorothioate oligonucleotides, i.e. tissue concentrations and tissue effects. The 2'-methoxyethyl modified phosphodiester oligonucleotide (ISIS 15163) was detected in greater concentrations in lung, but histologic alterations were limited to 1 animals in each of the single and multiple exposure groups.

It is intended that each of the patents, applications, printed publications, and other published documents mentioned or referred to in this specification be herein incorporated by reference in their entirety.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for enhancing cellular uptake of an oligonucleotide administered as an aerosol into a lung of a mammal by including 2'-O-methoxyethyl and 5-methylcytosine modifications in said oligonucleotide, said method comprising:

administering an aerosolized oligonucleotide into the lung of a mammal, wherein the aerosol particles have a size of about 1 to about 5 microns, wherein said oligonucleotide is 15 to 25 nucleotides in length, wherein at least 10 nucleosides in said oligonucleotide are 2'-O-methoxyethyl nucleosides, wherein each cytosine of said oligonucleotide is a 5-methylcytosine, and wherein said oligonucleotide is taken up by at least one cell type in the lung of the mammal.

2. The method of claim 1, wherein at least one internucleotide linkage within said oligonucleotide is a phosphorothioate linkage.

3. The method of claim 1, wherein said oligonucleotide is in an aqueous media.

4. The method of claim 1, wherein said oligonucleotide is in sterilized, pyrogen free water.

5. The method of claim 1, wherein said oligonucleotide is in a saline solution.

6. The method of claim 1, wherein said oligonucleotide is in a powder.

7. The method of claim 1, wherein each internucleotide linkage within said oligonucleotide is a phosphorothioate linkage.

8. The method of claim 1, wherein said oligonucleotide is 20 nucleotides in length, and said oligonucleotide is in a saline solution.

9. The method of claim 8, wherein each internucleotide linkage within said oligonucleotide is a phosphorothioate linkage.

10. The method of claim 8, wherein each nucleoside in said oligonucleotide is a 2'-O-methoxyethyl nucleoside.

11. The method of claim 1, wherein at least 10 to all but one nucleosides in said oligonucleotide are 2'-O-methoxyethyl nucleosides.

* * * * *

UNITED STATES PATENT AND TRADEMARK OFFICE
Certificate

Patent No. 8,153,602 B1                                                             Patented: April 10, 2012

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Clarence Frank Bennett, Carlsbad, CA (US); David J. Ecker, Encinitas, CA (US); Phillip Dan Cook, Fallbrook, CA (US); and Gregory E. Hardee, Del Mar, CA (US).

Signed and Sealed this Ninth Day of September 2014.

CHRISTOPHER M. BABIC
*Supervisory Patent Examiner*
Art Unit 1674
Technology Center 1600